United States Patent
Deininger et al.

(10) Patent No.: US 9,597,518 B2
(45) Date of Patent: Mar. 21, 2017

(54) IMPLANTABLE MEDICAL DEVICES AND RELATED CONNECTOR ENCLOSURE ASSEMBLIES UTILIZING CONDUCTORS ELECTRICALLY COUPLED TO FEEDTHROUGH PINS

(75) Inventors: Steven T. Deininger, Blaine, MN (US); Michael J. Baade, Zimmerman, MN (US); Rajesh V. Iyer, Eden Prairie, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 102 days.

(21) Appl. No.: 13/981,274

(22) PCT Filed: Jan. 20, 2012

(86) PCT No.: PCT/US2012/022086
§ 371 (c)(1),
(2), (4) Date: Sep. 9, 2013

(87) PCT Pub. No.: WO2012/102971
PCT Pub. Date: Aug. 2, 2012

(65) Prior Publication Data
US 2014/0049924 A1    Feb. 20, 2014

Related U.S. Application Data

(60) Provisional application No. 61/436,600, filed on Jan. 26, 2011.

(51) Int. Cl.
*A61N 1/00* (2006.01)
*A61N 1/375* (2006.01)
(Continued)

(52) U.S. Cl.
CPC .......... *A61N 1/375* (2013.01); *A61N 1/3754* (2013.01); *H05K 7/02* (2013.01); *H05K 7/1427* (2013.01);
(Continued)

(58) Field of Classification Search
CPC ........ A61N 1/375; A61N 1/3754; H05K 7/02; H05K 7/1427; Y10T 29/4913; Y10T 29/49208
See application file for complete search history.

(56) References Cited

U.S. PATENT DOCUMENTS 3,808,478 A    4/1974    Winkler
4,173,745 A    11/1979   Saunders et al.
(Continued)

FOREIGN PATENT DOCUMENTS

| WO | 2008100319 | 8/2008 |
|---|---|---|
| WO | 2010081139 | 7/2010 |
| WO | 2010117842 | 10/2010 |

OTHER PUBLICATIONS

International Search Report and Written Opinion, PCT/US2012/022086, Apr. 12, 2012.
(Continued)

*Primary Examiner* — George Manuel
(74) *Attorney, Agent, or Firm* — Withers & Keys, LLC

(57) ABSTRACT

Implantable medical devices include connector enclosure assemblies that utilize conductors electrically coupled to feedthrough pins that extend into a can where electrical circuitry is housed. The conductors may be coupled to the feedthrough pins and to capacitor plates within a filter capacitor by an electrically conductive bonding material and as a single bonding event during manufacturing. The base plate of the connector enclosure assembly may also include a ground pin. Ground capacitor plates may be present at a
(Continued)

ground aperture of the filter capacitor where the ground pin passes through so that the ground pin, a ground conductor, and the ground capacitor plate may be coupled. A protective cover may be provided for the connector enclosure assembly to enclose the conductors intended to extend into the can prior to the assembly being joined to the can. Conductors may be attached to a common tab that is subsequently removed.

27 Claims, 24 Drawing Sheets

(51) Int. Cl.
　　　*H05K 7/02*　　　(2006.01)
　　　*H05K 7/14*　　　(2006.01)
(52) U.S. Cl.
　　　CPC ...... *Y10T 29/4913* (2015.01); *Y10T 29/49208* (2015.01)

(56) References Cited

U.S. PATENT DOCUMENTS

| | | | |
|---|---|---|---|
| 4,254,775 A | 3/1981 | Langer | |
| 4,296,390 A | 10/1981 | Vanderheyden et al. | |
| 4,514,782 A | 4/1985 | Sakamoto et al. | |
| 4,995,389 A | 2/1991 | Harris | |
| 5,032,692 A | 7/1991 | DeVolder | |
| 5,040,091 A | 8/1991 | Yamaoka | |
| 5,176,136 A | 1/1993 | Giele | |
| 5,336,246 A | 8/1994 | Dantanarayana | |
| 5,470,345 A | 11/1995 | Hassler et al. | |
| 5,751,539 A | 5/1998 | Stevenson et al. | |
| 5,905,627 A * | 5/1999 | Brendel et al. | 361/302 |
| 6,083,640 A | 7/2000 | Lee et al. | |
| 6,118,672 A | 9/2000 | Yamauchi et al. | |
| 6,248,080 B1 | 6/2001 | Miesel et al. | |
| 6,297,943 B1 | 10/2001 | Carson | |
| 6,414,835 B1 | 7/2002 | Wolf et al. | |
| 6,498,951 B1 | 12/2002 | Larson et al. | |
| 6,529,103 B1 | 3/2003 | Brendel et al. | |
| 6,566,978 B2 | 5/2003 | Stevenson et al. | |
| 6,643,903 B2 | 11/2003 | Stevenson et al. | |
| 6,660,116 B2 | 12/2003 | Wolf et al. | |
| 6,721,602 B2 | 4/2004 | Engmark et al. | |
| 6,765,779 B2 | 7/2004 | Stevenson et al. | |
| 6,850,405 B1 | 2/2005 | Mileham et al. | |
| 6,936,899 B2 | 8/2005 | Juengling | |
| 6,987,428 B2 | 1/2006 | Marketkar et al. | |
| 7,035,076 B1 | 4/2006 | Stevenson | |
| 7,035,077 B2 | 4/2006 | Brendel | |
| 7,113,387 B2 | 9/2006 | Stevenson et al. | |
| 7,187,535 B1 | 3/2007 | Iyer et al. | |
| 7,187,974 B2 | 3/2007 | Haeg et al. | |
| 7,236,829 B1 | 6/2007 | Farazi et al. | |
| 7,242,982 B2 | 7/2007 | Singhal et al. | |
| 7,306,490 B1 | 12/2007 | Jeter | |
| 7,317,946 B2 | 1/2008 | Twetan et al. | |
| 7,363,090 B2 | 4/2008 | Halperin et al. | |
| 7,515,964 B1 | 4/2009 | Alexander et al. | |
| 7,590,450 B2 | 9/2009 | Iyer et al. | |
| 7,594,828 B2 | 9/2009 | Alexander et al. | |
| 7,630,768 B1 | 12/2009 | Coffed et al. | |
| 7,668,597 B2 | 2/2010 | Engmark et al. | |
| 7,693,576 B1 | 4/2010 | Lavie et al. | |
| 7,725,177 B2 | 5/2010 | Iyer | |
| 7,725,190 B2 | 5/2010 | Iyer et al. | |
| 7,748,093 B2 | 7/2010 | Iyer et al. | |
| 7,765,005 B2 | 7/2010 | Stevenson | |
| 7,803,014 B2 | 9/2010 | Sprain et al. | |
| 7,839,620 B2 | 11/2010 | Iyer et al. | |
| 7,917,218 B2 | 3/2011 | Iyer et al. | |
| 8,131,368 B2 | 3/2012 | Kast et al. | |
| 8,154,846 B2 | 4/2012 | Fauer et al. | |
| 8,494,649 B2 | 7/2013 | Stancer et al. | |
| 8,593,816 B2 | 11/2013 | Iyer et al. | |
| 8,604,341 B2 | 12/2013 | Barry et al. | |
| 9,138,821 B2 | 9/2015 | Brosnan et al. | |
| 2003/0139096 A1 | 7/2003 | Stevenson et al. | |
| 2003/0163171 A1 | 8/2003 | Kast | |
| 2004/0176815 A1 | 9/2004 | Janzig et al. | |
| 2004/0220627 A1 | 11/2004 | Crespi et al. | |
| 2006/0015150 A1 | 1/2006 | Rusin et al. | |
| 2007/0203530 A1 | 8/2007 | Hubing et al. | |
| 2007/0248881 A1 | 10/2007 | Scott et al. | |
| 2008/0033500 A1 | 2/2008 | Strother et al. | |
| 2008/0246231 A1 | 10/2008 | Sjostedt et al. | |
| 2010/0009512 A1 | 1/2010 | Fishburn | |
| 2010/0177458 A1 | 7/2010 | Iyer | |
| 2011/0029028 A1 | 2/2011 | Peters et al. | |
| 2012/0203292 A1 | 8/2012 | Deininger | |
| 2012/0203314 A1 | 8/2012 | Deininger | |
| 2014/0043739 A1 | 2/2014 | Deininger | |

OTHER PUBLICATIONS

International Search Report and Written Opinion, PCT/US2012/022071, Apr. 20, 2012.
U.S. Appl. No. 13/981,264, filed Sep. 12, 2013.
U.S. Appl. No. 13/449,428, filed Apr. 18, 2012.
U.S. Appl. No. 13/449,446, filed Apr. 18, 2012.
U.S. Appl. No. 13/449,428, Office Action dated Feb. 10, 2015.
U.S. Appl. No. 13/449,428, Response filed May 11, 2015.
U.S. Appl. No. 13/449,428, Final Office Action dated Jul. 8, 2015.
U.S. Appl. No. 13/449,428, Response Filed Oct. 16, 2015.
U.S. Appl. No, 13/449,428, Advisory Action dated Oct. 19, 2015.
U.S. Appl. No. 13/449,428, RCE Response filed Nov. 6, 2015.
U.S. Appl. No. 13/449,446, Office Action dated Feb. 10, 2015.
U.S. Appl. No. 13/449,446, Response filed May 11, 2015.
U.S. Appl. No. 13/449,446, Final Office Action dated Aug. 6, 2015.
U.S. Appl. No. 13/449,446, Response Filed Oct. 6, 2015.
U.S. Appl. No. 13/449,446, Advisory Action dated Oct. 19, 2015.
U.S. Appl. No. 13/449,446, RCE Response filed Nov. 6, 2015.
U.S. Appl. No. 12/847,830 filed Jul. 30, 2010.
U.S. Appl. No. 12/847,830, Restriction Requirement dated Nov. 16, 2012.
U.S. Appl. No. 12/847830 Response to Restriction Requirement dated Dec. 12, 2012.
U.S. Appl. No. 12/847,830, Office Action dated Dec. 19, 2012.
U.S. Appl. No. 12/847,830, Response to Office Action dated Aug. 26, 2013.
U.S. Appl. No. 12/847,830, Final Office Action dated Oct. 31, 2013.
U.S. Appl. No. 12/847,830, Appeal Pre-Brief Conference Request dated Jan. 31, 2014.
U.S. Appl. No. 12/847,830, Appeal Brief dated Apr. 4, 2014.
U.S. Appl. No. 12/847,830, Answer to Appeal Brief dated Jun. 18, 2014.
U.S. Appl. No. 12/847,830, Reply Brief dated Aug. 18, 2014.
U.S. Appl. No. 13/449,446, Office Action dated Feb. 8, 2016.
U.S. Appl. No. 13/449,428, Office Action dated Feb. 22, 2016.
U.S. Appl. No. 13/981,264, Notice of Allowance dated Apr. 11, 2016.
Standard Specification for Stainless Steel Sheet and Strip for Surgical Implants:, ASTM, desingation F56-52.
Titanium Ti-6A1-4V (Grade 5) Annealed, ASM.
U.S. Appl. No. 13/449,446—Response to Office Action dated May 9, 2016.
U.S. Appl. No. 13/449,428—Response to Office Action dated May 23, 2016.
U.S. Appl. No. 13/981,264—Office Action dated Jul. 6, 2016.
EP 12702925.4 Examination Report—Jun. 29, 2016.

* cited by examiner

IMPLANTABLE MEDICAL DEVICES AND RELATED CONNECTOR ENCLOSURE ASSEMBLIES UTILIZING CONDUCTORS ELECTRICALLY COUPLED TO FEEDTHROUGH PINS

TECHNICAL FIELD

Embodiments are related to implantable medical devices and connector assemblies for implantable medical devices. More particularly, embodiments are related to implantable medical devices and connector enclosure assemblies that use conductors electrically coupled to feedthrough pins.

BACKGROUND

Implantable medical devices conventionally include a connector enclosure where the connectors mate to medical lead contacts and further include a can that houses the electrical circuitry. In these conventional devices, a top plate seals the can and exposes feedthrough pins that extend out of the can. The connector enclosure sits atop the top plate and receives the feedthrough pins where they connect to lead frame conductors that interconnect the feedthrough pins to the electrical connectors. Thus, during manufacturing, the feedthrough assembly is a part of the can assembly and the connector assembly is then added to complete the device, typically by creating the electrical connections for the connector assembly and then forming the connector enclosure over the connections using a polymer.

Within the can of the convention medical device, the feedthrough pins pass through and are bonded to a filter capacitor that provides a capacitive coupling to the can to filter out unwanted electromagnetic interference signals from entering into the device. The feedthrough pins including a pin dedicated for establishing an electrical ground for the electrical circuitry within the can would then be laser welded to a feedthrough contact. A flexible circuit portion interconnects the feedthrough contact to the circuit board that contains the electrical circuitry of the device.

This conventional approach has less appeal as device designs continue to get smaller. The amount of space required to bond the feedthrough pins to the filter capacitor and then bond the feedthrough pins to the underlying feedthrough contact limit the amount of miniaturization that may occur in the area of the feedthrough connections within the can. Furthermore, these feedthrough manufacturing operations require valuable time and resources to accomplish. In some cases, even the flexible circuit may be an undesirable cost in terms of resources and space requirements.

SUMMARY

Embodiments address issues such as these and others by providing various features related to interconnections of the feedthrough pins to the electrical circuitry within the can. In one or more embodiments, the feedthrough pins and filter capacitor may be included in the manufacture of a connector enclosure assembly that is subsequently mounted to the can. In particular, embodiments may provide an interconnection of a feedthrough pin, a filter capacitor, and a conductor intended to extend into the can with an electrically conductive bonding material such as solder and the bond may occur as a single event of the manufacturing process. Embodiments may provide features such as ground pins that are integral to a base plate of the connector enclosure assembly. Embodiments may provide features such as a support body that partially contains the conductor intended to extend into the can. Embodiments may provide features such as an internal ground plate within the filter capacitor that establishes an interconnection to the ground pin. Embodiments may provide features such as a protective body that attaches to the connector enclosure assembly during a period prior to attachment of the assembly to the can to enclose and protect the conductor that is intended to extend into the can. Embodiments may provide conductors attached to a common tab that is later removed during assembly.

Embodiments provide an implantable medical device that includes a connector enclosure including a base plate having an aperture, the connector enclosure housing at least one electrical connector. A can is coupled to the base plate, the can housing electrical circuitry. A filter capacitor is coupled to the base plate, the filter capacitor having an aperture and having capacitor forming plates including a ground plate, the ground plate being electrically coupled to the can. A feedthrough pin is electrically coupled to the electrical connector within the connector enclosure, the feedthrough pin extending through the aperture in the base plate and being present in the vicinity of the aperture in the filter capacitor. A conductor has a first end being present in the vicinity of the aperture within the filter capacitor and has a second end extending into the can and electrically coupled to the electrical circuitry. An electrically conductive bonding material is present within the aperture of the filter capacitor and creates an electrically conductive bond among the conductor, the feedthrough pin, and at least one of the capacitor forming plates other than the ground plate.

Embodiments provide a method of manufacturing a connector enclosure assembly of an implantable medical device that involves providing a connector enclosure including a base plate having an aperture, the connector enclosure housing at least one electrical connector. The method further involves providing a filter capacitor coupled to the base plate, the filter capacitor having an aperture and having capacitor forming plates; providing a feedthrough pin electrically coupled to the electrical connector within the connector enclosure, the feedthrough pin extending through the aperture in the base plate and being present in the vicinity of the aperture in the filter capacitor; and providing a conductor with a first end being present in the vicinity of the aperture within the filter capacitor and with a second end extending away from the filter capacitor. Additionally, the method involves creating a single electrically conductive bond among the conductor, the feedthrough pin, and at least one of the capacitor forming plates.

Embodiments provide an implantable medical device that includes a connector enclosure including a base plate having an aperture and an integral ground pin, the connector enclosure housing at least one electrical connector. A can is coupled to the base plate, the can housing electrical circuitry. A filter capacitor is coupled to the base plate, the filter capacitor having an aperture and having capacitor forming plates including a ground plate, the ground plate being electrically coupled to the ground pin of the base plate. A feedthrough pin is electrically coupled to the electrical connector within the connector enclosure, the feedthrough pin extending through the aperture in the base plate and being electrically coupled to a filter capacitor other than the ground plate. A first conductor has a first end being electrically coupled to the feedthrough pin and the filter capacitor other than the ground plate and has a second end extending into the can and electrically coupled to the electrical circuitry. A ground conductor has a first end being electrically coupled to the integral ground pin and has a second end extending into the can and electrically coupled to the electrical circuitry.

Embodiments provide an implantable medical device that includes a connector enclosure including a base plate having an aperture, the connector enclosure housing at least one electrical connector. A can is coupled to the base plate, the can housing electrical circuitry. A filter capacitor is coupled to the base plate, the filter capacitor having an aperture and having capacitor forming plates including a ground plate, the ground plate being electrically coupled to the can. A feedthrough pin is electrically coupled to the electrical connector within the connector enclosure, the feedthrough pin extending through the aperture in the base plate and being electrically coupled to at least one filter capacitor. A support body has a coupling to the base plate, the support body having a conductor passing through, the conductor having a first end extending from the support body on one side and a second end extending from the support body on another side, the first end being electrically coupled to the filter capacitor and the feedthrough pin and the second end extending into the can and being electrically coupled to the electrical circuitry.

Embodiments provide an implantable medical device that includes a connector enclosure including a base plate having an aperture and a ground pin, the connector enclosure housing at least one electrical connector. A can is coupled to the base plate, the can housing electrical circuitry. A filter capacitor is coupled to the base plate, the filter capacitor having a ground aperture and having capacitor forming plates including a ground plate, the ground plate extending to the ground aperture. A feedthrough pin is electrically coupled to the electrical connector within the connector enclosure, the feedthrough pin extending through the aperture in the base plate and being electrically coupled to a filter capacitor other than the ground plate. A first conductor has a first end being electrically coupled to the feedthrough pin and the filter capacitor other than the ground plate and has a second end extending into the can and electrically coupled to the electrical circuitry. A ground conductor has a first end being electrically coupled to the integral ground pin and the ground plate and has a second end extending into the can and electrically coupled to the electrical circuitry. An electrically conductive bonding material is present within the ground aperture of the filter capacitor and creates an electrically conductive bond among the ground conductor, the ground pin, and the ground plate.

Embodiments provide a connector enclosure assembly for an implantable medical device that includes a connector enclosure including a base plate having an aperture, the connector enclosure housing at least one electrical connector. A filter capacitor is coupled to the base plate, the filter capacitor having an aperture and having capacitor forming plates. A feedthrough pin is electrically coupled to the electrical connector within the connector enclosure, the feedthrough pin extending through the aperture in the base plate and being present in the vicinity of the aperture in the filter capacitor. A conductor has a first end being present in the vicinity of the aperture within the filter capacitor and has a second end extending away from the filter capacitor, the first end being electrically coupled to the filter capacitor and the feedthrough pin. A protector body is affixed to the base plate, the protector body enclosing the conductor while having an aperture providing access to the conductor.

Embodiments provide a connector enclosure assembly for an implantable medical device. The connector assembly includes a connector enclosure including a base plate having a plurality of apertures and further includes a filter capacitor coupled to the base plate, the filter capacitor having a plurality of apertures and having capacitor forming plates. The connector enclosure assembly includes a plurality of feedthrough pins extending through the apertures in the base plate and in the filter capacitor and also includes a plurality of conductors with a first end of each conductor having an annular ring that surrounds a corresponding feedthrough pin in proximity to the filter capacitor with a second end of the plurality of conductors extending away from the filter capacitor and being joined to a common tab.

Embodiments provide a method of manufacturing a connector enclosure assembly of an implantable medical device. The method involves providing a connector enclosure including a base plate having a plurality of apertures and providing a filter capacitor coupled to the base plate, the filter capacitor having a plurality of apertures and having capacitor forming plates. The method further involves providing a plurality of feedthrough pins extending through corresponding apertures in the base plate and in the filter capacitor. Additionally, the method involves positioning a plurality of conductors with a first end of each conductor having an annular ring that surrounds a corresponding feedthrough pin in proximity to the filter capacitor with a second end of the plurality of conductors extending away from the filter capacitor and wherein the plurality of conductors are positioned by the second ends having a connection to a common tab.

DETAILED DESCRIPTION

Embodiments provide implantable medical devices that include various features related to the electrical connectivity of a connector enclosure assembly containing electrical connectors to a can that houses electrical circuitry. For example, the features may include feedthrough pins that are interconnected to conductors and filter capacitors via a common electrically conductive bonding material, where the electrical bond that provides the interconnection may be done as a single step during manufacturing. As other examples, the features may include an integral ground pin in a base plate and/or a filter capacitor that provides a ground plate that interconnects to a ground pin. Other examples include the apertures within the filter capacitor that receive both the feedthrough pin and a conductor intended to extend into the can, where those apertures may have a shape such as a keyhole, and/or the filter capacitor may include an asymmetric shape that is received within a matching recess of the base plate. Additional examples include a protective body that attaches to the base plate to protect the conductors that are intended to extend into the can prior to the connector enclosure assembly being mounted to the can. Furthermore, in some embodiments, the conductors may be attached to a common tab that is later removed during assembly.

Figure 1:
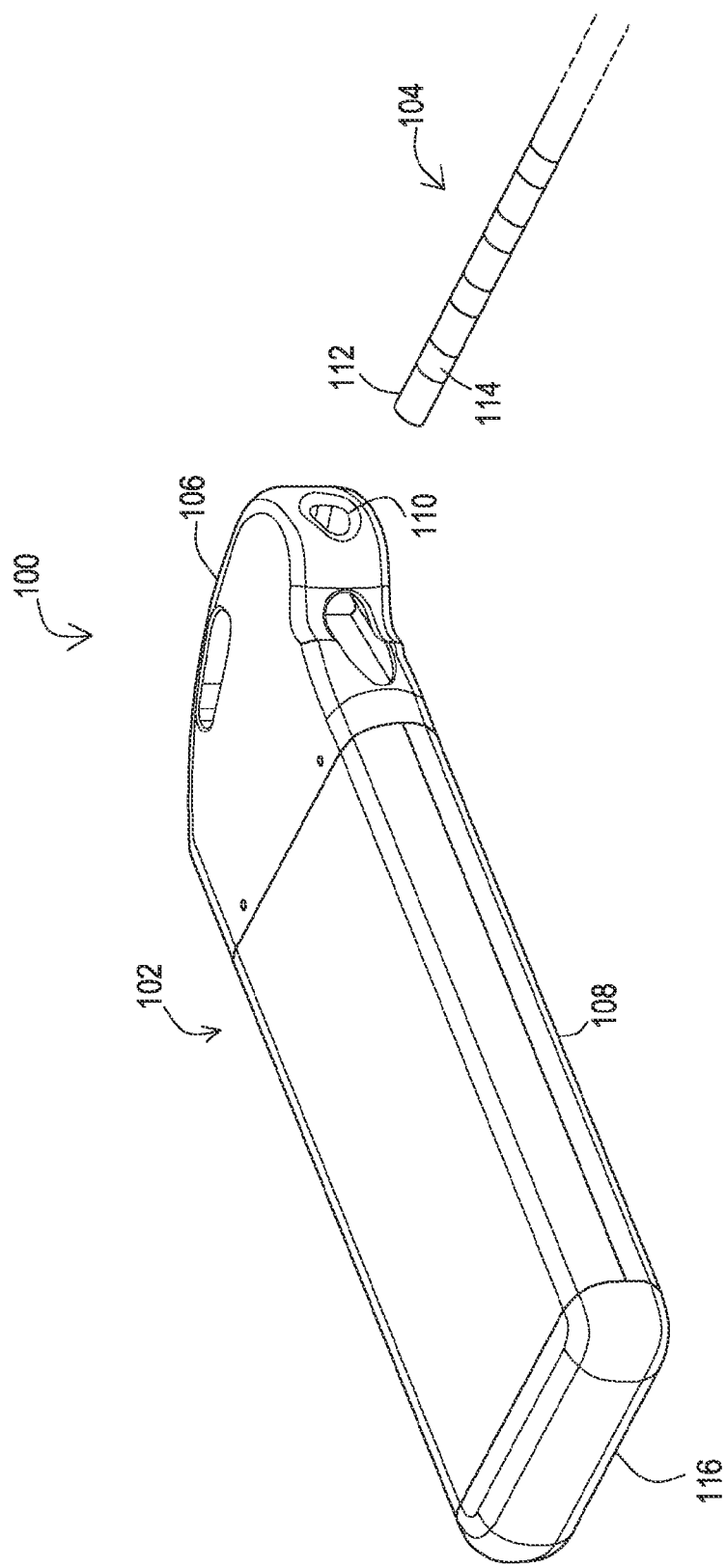
FIG. 1 shows an implantable medical system according to various embodiments.

FIG. 1 shows an implantable medical device (IMD) system 100 that includes an IMD 102 and an implantable medical lead 104. The IMD 102 may be of various types, such as a device for producing electrical stimulation and/or for sensing physiological signals for various medical applications such as neurological or cardiac therapy. The implantable medical lead 104 includes a proximal end 112 of a lead body where a series of electrical contacts 114 are located. Each electrical contact has a corresponding conductor within the lead body that extends to a distal end (not shown) where a series of electrodes are present.

The implantable medical lead 104 is implanted into the body with the distal end being routed to a desired location such that the electrodes contact the tissue of interest. The proximal end 112 is inserted into a connector enclosure assembly 106 of the IMD 102 via an entryway 110. Within the connector enclosure assembly 106, electrical connectors make contact with each of the contacts 114. Electrical circuitry within the can 108 provides stimulation signals and/or monitors for sensed signals by being electrically connected to the connectors within the connector enclosure assembly 106. The electrical circuitry is thereby also connected to the electrodes at the distal end of the implantable medical lead 104 such that the stimulation signals may be provided to tissue at the electrodes and/or sensed signals may be obtained from the tissue.

Figure 2:
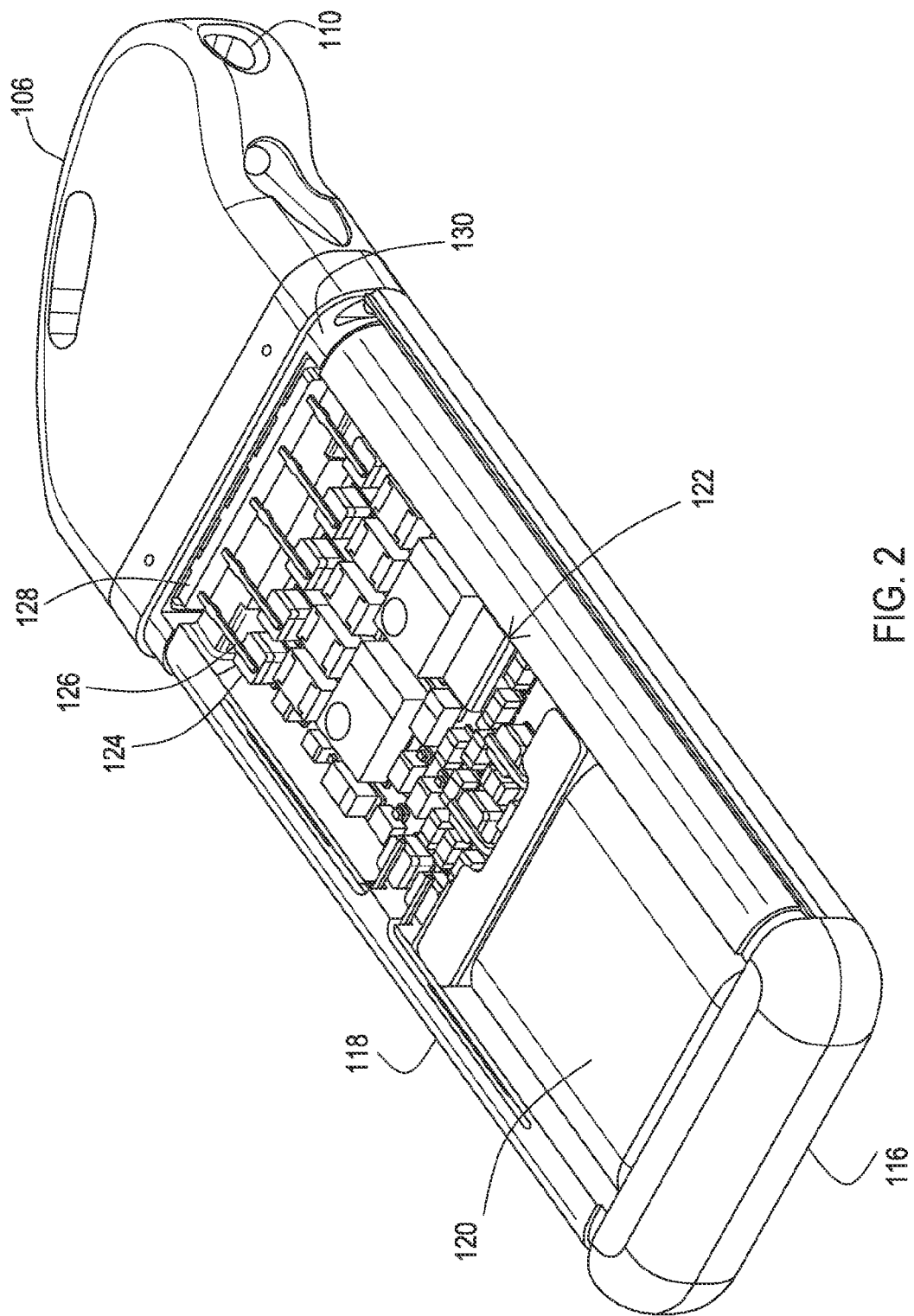
FIG. 2 shows an example of implantable medical device with a portion of a can removed to reveal interior features.

In this particular example, the can 108 relies on separate components to create a hermetically sealed enclosure for the electrical circuitry. Namely, the can 108 relies on a bottom cap 116 that may be welded in place or may be formed integrally with the can 108 and relies on a base plate 130 which is shown in FIG. 2 that is a component of the connector enclosure assembly 106 in this example. During manufacturing, the connector enclosure assembly 106 is joined to the can 108 by the base plate 130 being bonded such as by a weld to the top edge of the can 108. The can 108, bottom cap 116, and the connector assembly 106 including the base plate 130 may be made of rigid biocompatible materials such as various grades of titanium.

FIG. 2 shows the IMD 102 with one side of the can 108 removed to reveal inner components. In this example, the IMD 102 includes a battery 120 and electrical circuitry 122 housing within an isolation cup 118. The isolation cup 118 may securely hold the components within the can 108 while isolating the components from contact with the can 108. The isolation cup 118 may be constructed of an insulator such as a liquid crystal polymer.

In this particular example, the electrical circuitry 122 includes electrical contact pads 124. Conductors 126 that extend from the connector enclosure assembly 106 align with and are bonded to the electrical contact pads 124 such as by soldering or a spot weld or the like during assembly of the IMD 102. As discussed in more detail below, these conductors 126 provide electrical connectivity between the electrical circuitry 122 and feed through pins, where the feedthrough pins provide electrical connectivity to the electrical connectors within the connector enclosure assembly 106.

As the conductors 126 extend from the feedthrough pins 136 to the contact pads 124 in this example, there is no need for a flexible circuit to provide the interconnection. Accordingly, the structure for interconnecting the flexible circuit to the feed through pins is omitted.

The conductors 126 pass through a support body 128 that is affixed to the underside of the base plate 130. The support body 128 holds the conductors in proper positioning for interconnection to the feedthrough pins of the connector enclosure assembly 106 and also in proper position for bonding to the contact pads 124 of the electrical circuitry 122 within the can 108. The support body 128 is discussed in more detail below with reference to FIG. 10. A discussion of the assembly of the device 102 is also discussed in more detail below.

Figure 3:
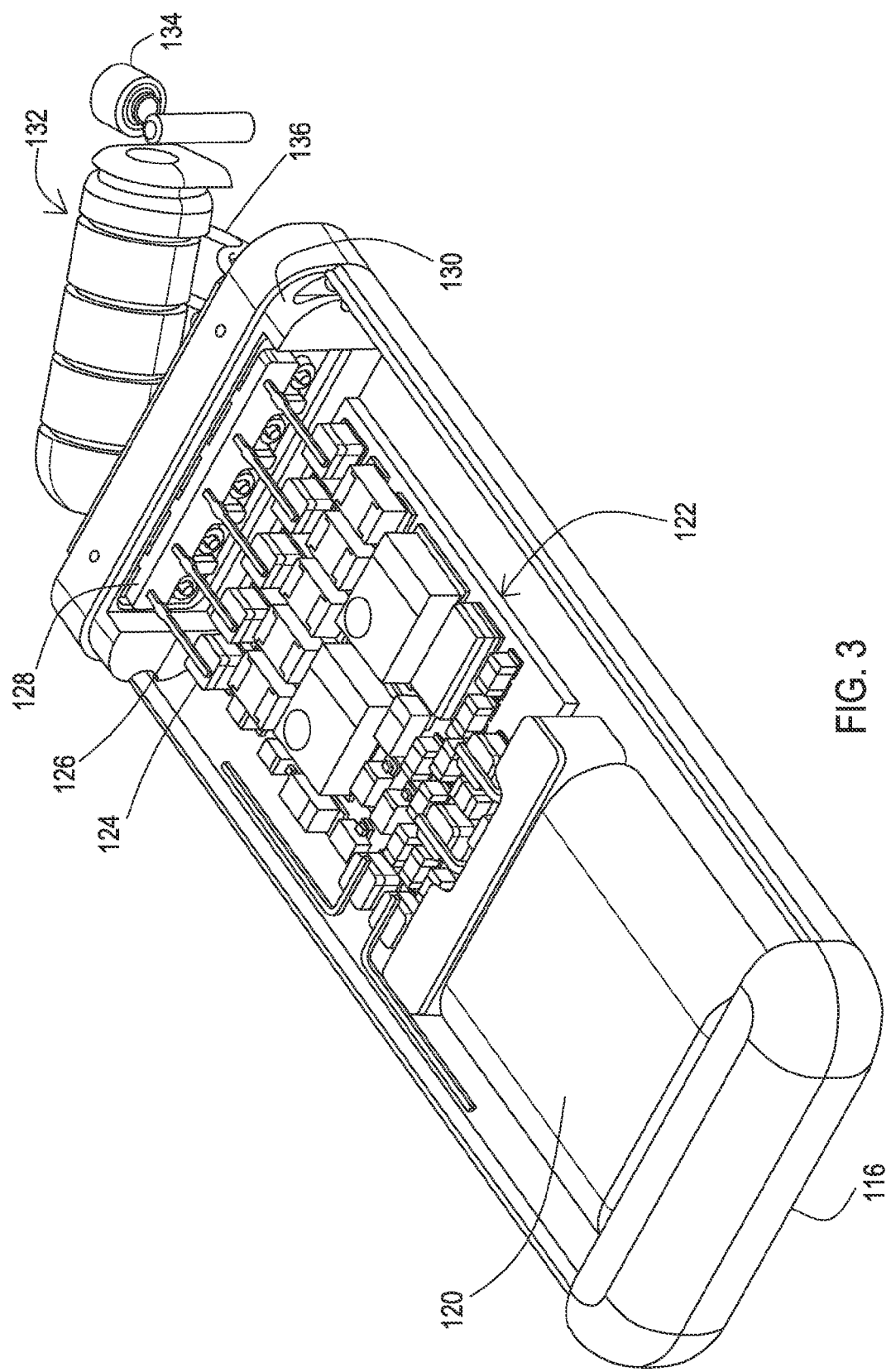
FIG. 3 shows the implantable medical device with a connector enclosure removed to further reveal interior features.

FIG. 3 shows the IMD 102 with the connector enclosure removed to reveal the set of electrical connectors 132, a set screw 134, and feedthrough pins 136. The connector enclosure which has been removed may be constructed of a polymer that is molded over the components shown in FIG. 3 or may be machined from a metal. For examples where the connector enclosure is machine from metal, passageways are include that allow the feedthrough pins 136 to avoid contact with the metal enclosure walls, while the set of connectors 132 are surrounded by an insulator separating the connectors 132 from the metal enclosure walls. Furthermore, the interior of the connector enclosure may be filled with an insulator such as a silicone to further insulate conductors from the metal enclosure. In this particular example, the feedthrough pins extend up to the connectors 132 and make electrical connection with the connectors 132. It will be appreciated that in other examples, there may be an intervening electrically conductive structure to interconnect the feedthrough pins 136 and the connectors 132.

Figure 4:
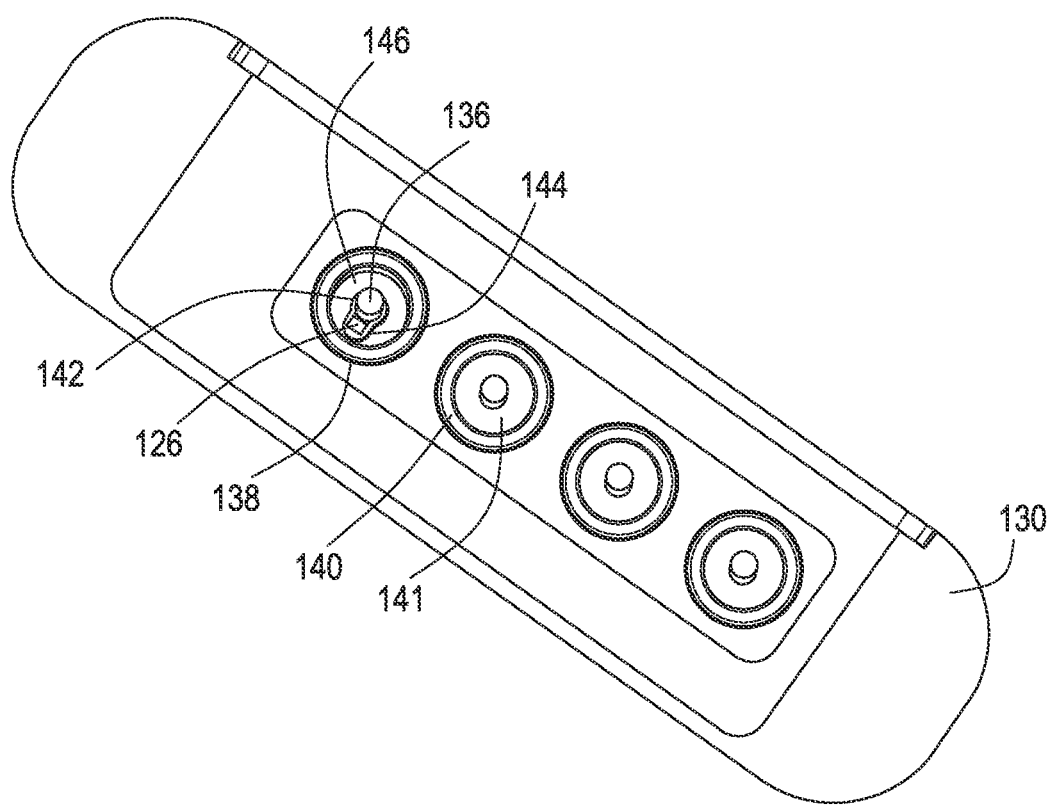
FIG. 4 shows a top view of a base plate and feedthrough pins of a connector enclosure assembly of the implantable medical device.

FIG. 4 shows a top view of the connector enclosure assembly with the connector enclosure and the connectors 132 removed to reveal the top of the base plate 130. The feedthrough pins 136 can be seen rising from apertures 138 within the base plate 130. These apertures 138 may include a ferrule 140 or other similar structure that includes an insulator 141 such as a nonconductive polymer which surrounds the feedthrough pin 136 to support the feedthrough pin within the aperture 138, create a seal between the feedthrough pin 136 and the base plate 130, and to isolate the feedthrough pin 136 from contact with the base plate 130.

In FIG. 4, the insulator material 141 has been removed to reveal a filter capacitor 146 that lies underneath the base plate 130. The filter capacitor 146 may be used to provide a filtered feedthrough by including capacitively coupled plates, where the interconnected feedthrough pin 136 and conductor 126 are capacitively coupled to ground to remove EMI signals from entering device. This capacitive coupling is discussed in more detail below.

The filter capacitor 146 has an aperture 142 that allows the feedthrough pin 136 to pass through. In this particular example, the aperture 142 also includes a region 144 that allows the conductor 126 to enter into the aperture 142 such that the feedthrough pin 136 and conductor 126 are adjacent within the aperture 142. In this particular example, the region is smaller than the portion of the aperture 142 where the feedthrough pin 136 passes such that the aperture 142 has a keyhole shape.

The conductor 126 and the feedthrough pin 136 are in the vicinity of one another as well as in the vicinity of the aperture 142. In this particular example, both the conductor 126 and the feedthrough pin 136 are present within the aperture 142. Because the conductor 126 and the feedthrough pin 136 are in the vicinity of one another and in the vicinity of the aperture 142, the conductor 126 and the feedthrough pin 136 may be bonded together as well as to the filter capacitor 146 via a single bonding event, as opposed to a separate bonding event for the conductor and a separate bonding even for the feedthrough pin. Furthermore, the non-ground capacitor plates within the filter capacitor 146 may be present at the non-ground aperture 142 such that the bond may also occur with the non-ground capacitor plates as shown below in FIG. 8. Thus, a single bonding event creates an electrical connection among the feedthrough pin 136, the conductor 126, and the non-ground capacitor plate of the filter capacitor 146 while creating a physical connection among feedthrough pin 136, conductor 126, and filter capacitor 146.

The filter capacitor 146 may be a ceramic material with conductive layer within to provide the capacitance. The aperture 142 may have a border such as silver-palladium or Ni—Au plating or the like sputtered or otherwise attached to the ceramic about the aperture 142 so that an electrically conductive bonding material may be used to bond the conductor 126, the feedthrough pin 136, and the filter capacitor 146 together. For example, a solder joint 148 may be created at the junction of the conductor 126, the feedthrough pin 136, and the filter capacitor 146.

Figure 5A:
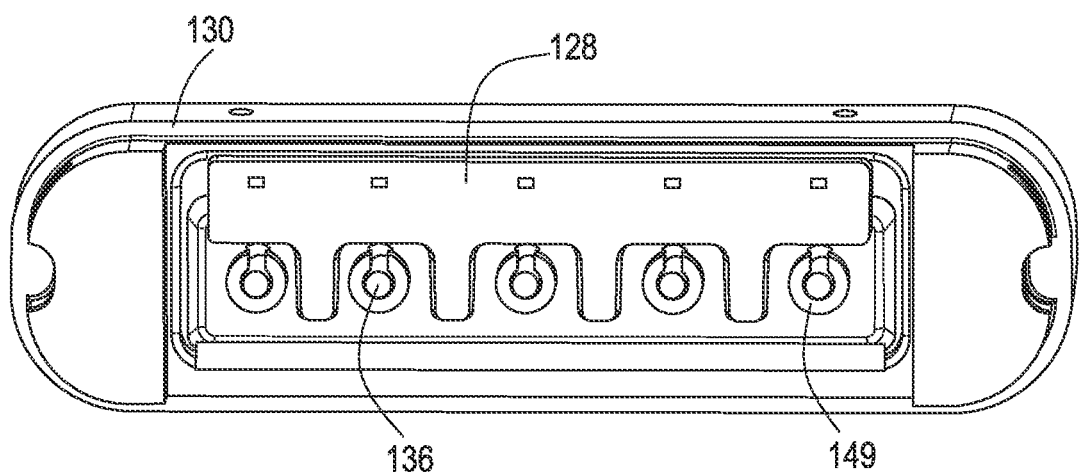
FIGS. 5A and 5B show a bottom view of a base plate, feedthrough pins, and related conductors of a connector enclosure assembly of the implantable medical device.
Figure 5B:
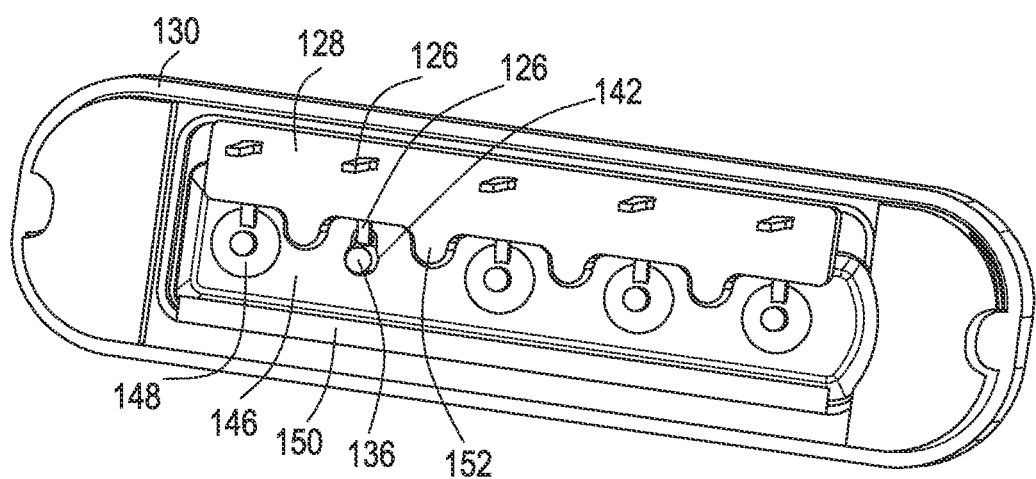

FIGS. 5A and 5B show the underside of the base plate 130 with the connector enclosure assembly 106 being free from the can 108. A solder joint 148 is present at the junction of a conductor, a pin, and the filter capacitor 146. The filter capacitor 146 itself may be mechanical and electrically bonded to the base plate 130 via a bonding material 150, such as solder where the edge of the filter capacitor has a metal sputtered in place or otherwise attached to the ceramic such that the bonding material 150 such as solder bonds to the filter capacitor 146 and to the base plate 130.

FIG. 5A shows the underside prior to the bond being created among the feedthrough pin 136, conductor 126, and filter capacitor 146. The bonding material, such as solder, may have a preformed shape. In this example, the preformed shape 149 includes a split where the conductor 126 is positioned prior to heating the preformed shape 149. Upon heating, the preformed shape 149 becomes the bonded material 148 of FIG. 5B.

For purposes of illustration, in FIG. 5B the solder is omitted for one of the junctions of the feedthrough pin 136 and conductor 126 to reveal the keyhole shaped aperture 142 with the feedthrough pin 136 and conductor 126 being present at the aperture 142. FIG. 5B also shows one view of the alignment of the support body 128 and the filter capacitor 146. In this example, the support body 128 includes protrusions 152 that occur between each of the apertures 142 of the filter capacitor 146.

Figure 6:
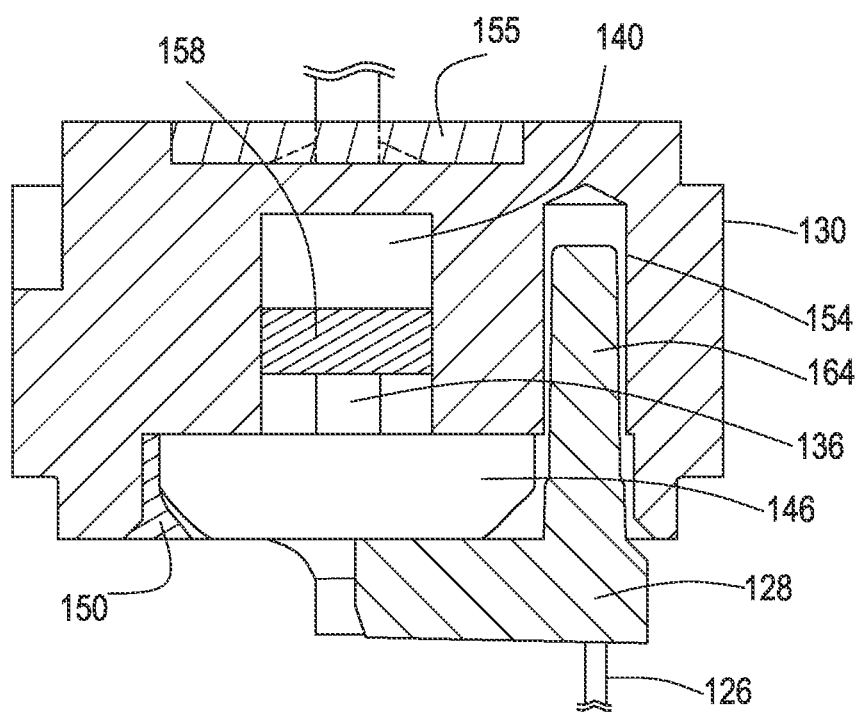
FIG. 6 shows a front-to-back cross-sectional view taken through the base plate to reveal a mounting post of a support body of the connector enclosure assembly.

FIG. 6 shows a cross-sectional view further illustrating the relationship of the support body 128 to the filter capacitor 146 and the base plate 130. Here it can be seen that the support body 128 of this example includes a mounting post 164. The mounting post 164 is press fit into a cavity 154 within the base plate 130. This press fit holds the support body 128 in a fixed position with respect to the base plate 130, and also provides additional support for the filter capacitor 146 as the support body 128 contacts the underside of the filter capacitor 146.

FIG. 6 also shows the ferrule 140 that separates the nonconductive polymer 141 not shown in this view and the feedthrough pin 136 from the base plate 130. FIG. 6 also shows a separate insulator 158 that is present beneath the ferrule 140 and that is located between the feedthrough pin 136 and the base plate 130. Additionally, a coating of a nonconductive material 155 such as a medical adhesive can be seen atop the base plate 130 covering the area where the feedthrough pins 136 pass into the base plate 130.

Figure 7:
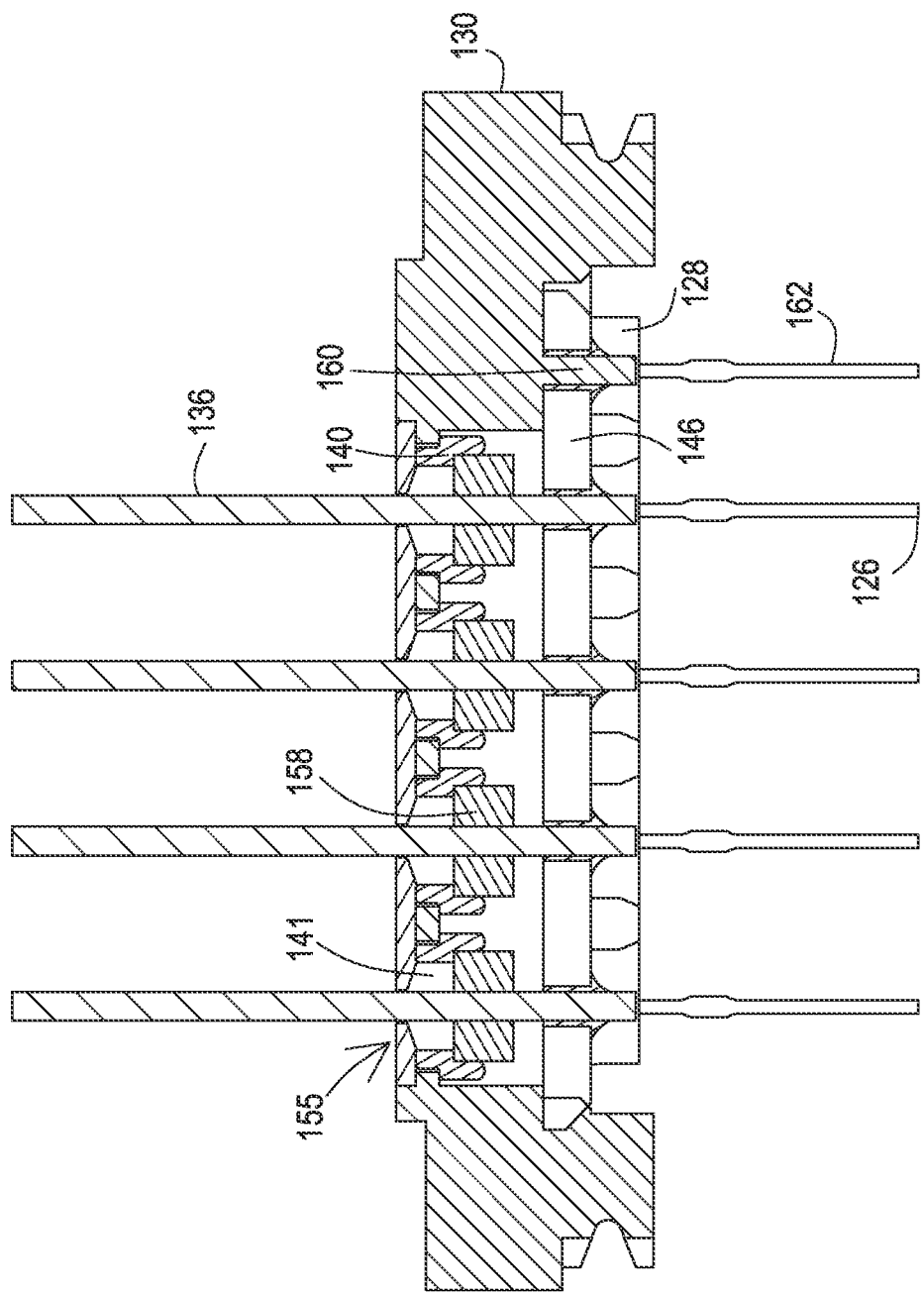
FIG. 7 shows a side-to-side cross-sectional view taken through the base plate to reveal an integral ground pin of the base plate as well as the feedthrough pins and related conductors of the support body.

FIG. 7 shows another cross-sectional view of the base plate 130 and the filter capacitor 146. FIG. 7 shows another view of the relationship between the medical adhesive 155, the ferrule 140, the nonconductive polymer 141, the insulator 158, and the feedthrough pin 136. This view also reveals that the base plate 130 of this particular example includes an integral ground pin 160. This integral ground pin 160 may be machined as a feature of the base plate 130. As an alternative, a ground pin 160 could be welded or otherwise attached to the base plate 130.

A ground conductor 162 is interconnected within the ground pin 160 via an electrically conductive bond at a ground aperture of the filter capacitor 146. Thus, the electrically circuitry 122 has a ground to the base plate 130 which will ultimately be electrically connected to the can 108 upon welding of the base plate 130 to the can 108. Furthermore, the ground aperture of the filter capacitor 146 may include the ground plates of the capacitive coupling present within the filter capacitor 146 such that the electrically conductive bond also occurs with the ground plates, which is discussed in more detail below with reference to FIG. 9. Therefore, in a single bonding event, an electrically conductive bond may occur among the ground pin 160, a ground conductor 162, and the ground capacitor plate of the filter capacitor 146 while a physical bond may also occur among the ground pin 160, the ground conductor 162, and the filter capacitor 146.

Figure 8:
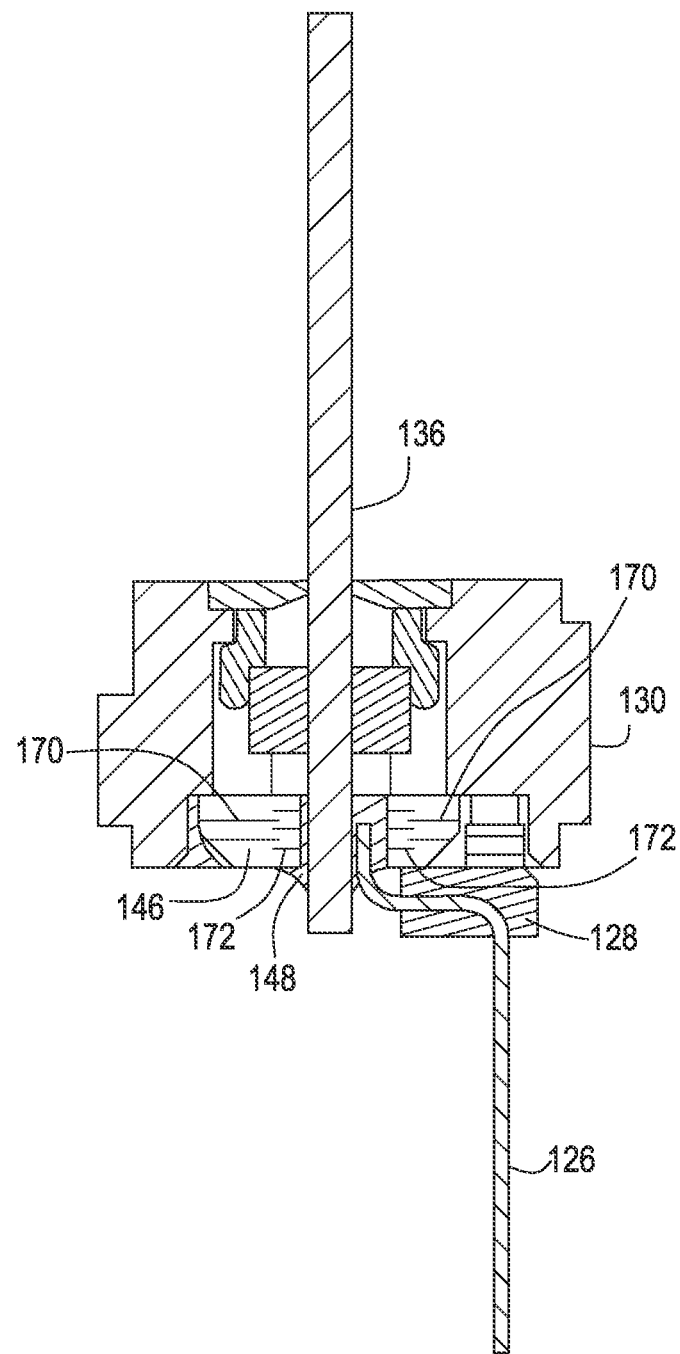
FIG. 8 shows a front-to-back cross-sectional view taken through the base plate to reveal the interconnection of the feedthrough pin, related conductor, and filter capacitor.

FIG. 8 shows another cross-sectional view which illustrates an example where the feedthrough pin 136 and the conductor 126 are both present within the aperture 142 of the filter capacitor 146. Here, the non-ground capacitor plates 172 and the ground capacitor plates 170 can be seen within the filter capacitor 146, and the electrically conductive bond material 148 such as solder can also be seen filling the aperture and creating the electrical connection between the feedthrough pin 136, the conductor 126, and the non-ground capacitor plates 172. As can also be seen the ground capacitor plates 170 are electrically connected to the base plate 130.

Figure 9:
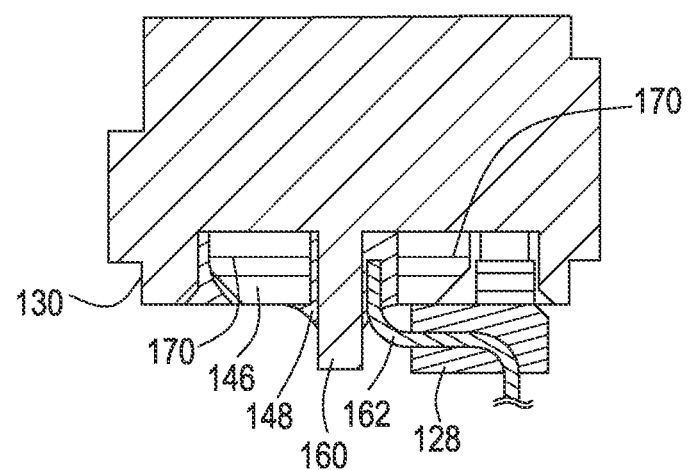
FIG. 9 shows a front-to-back cross-sectional view taken through the base plate to reveal the interconnection of the integral ground pin, related conductor, and filter capacitor.

FIG. 9 shows another cross-sectional view which reveals details of the ground aperture of the filter capacitor 146. Here it can be seen that the ground plates 170 are present at the ground aperture of the filter capacitor 146 such that the ground pin 160, ground conductor 162, and the ground plates 170 are electrically interconnected via the electrically conductive bonding material 148. In this case, there is a direct ground path from the electrical circuitry 122 to the ground plates 170 through this junction established by the electrically conductive bonding material 148.

Figure 10:
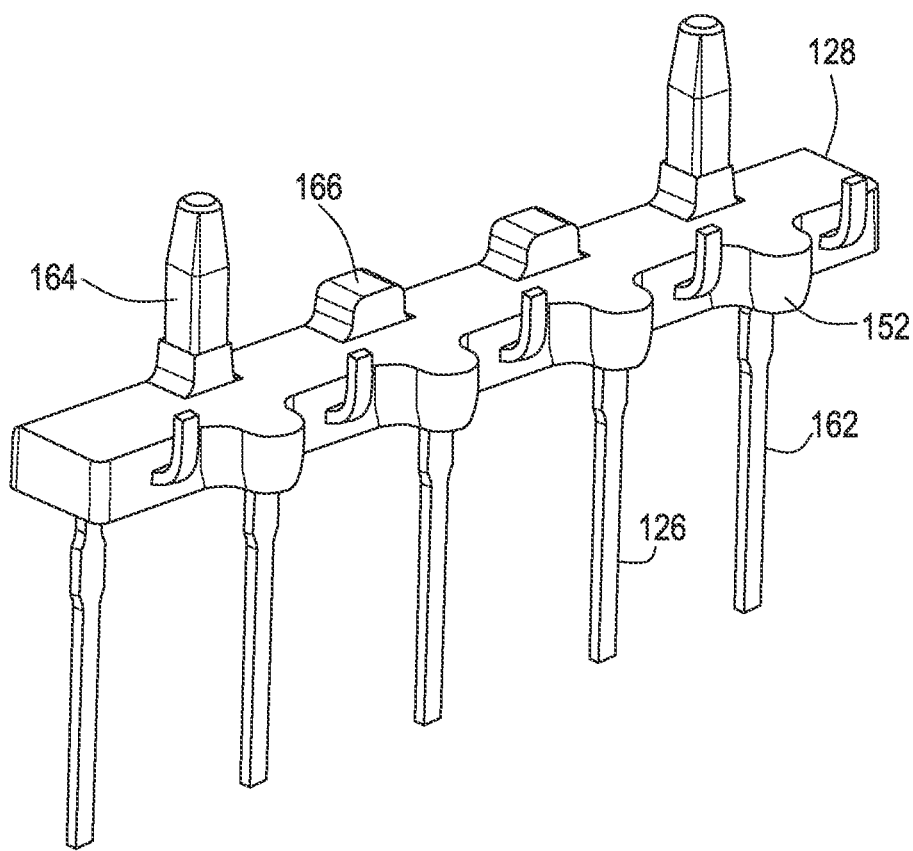
FIG. 10 shows the support body and conductors that pass therethrough.

FIG. 10 shows details of the support body 128 and conductors 126, 162. Here it can be seen that the conductors pass through the support body 128, such as into one side and out another. In this case, the conductors 126, 162 pass through a bottom side and out a front side but it will be appreciated that the conductors 126, 162 could pass through other sides of the support body 128. As the support body 128 contains the conductors, the support body 128 is constructed of an insulator such as polyether ether ketone (PEEK).

The support body 128 includes the posts 164 as well as protrusions 166 that abut the base plate 130 to create proper spacing between the support body 128 and the base plate 130 where the filter capacitor 146 resides. The support body also includes the protrusions 152 which properly position the support body 128 by abutting the filter capacitor 146 to align the interfacing surfaces.

Figure 11:
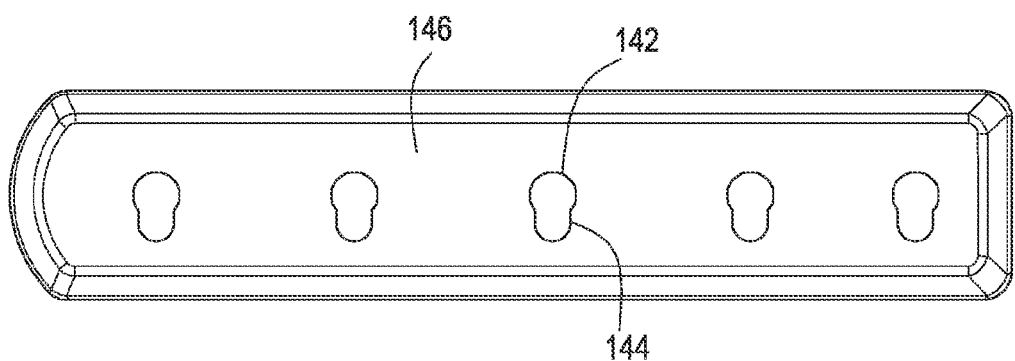
FIG. 11 shows the filter capacitor and related apertures.

FIG. 11 shows the filer capacitor 146. This view further illustrates the asymmetric shape of this particular example as discussed above. This view also further illustrates the apertures 142 of this example, and particularly the keyhole shape of the apertures 142 having the smaller diameter portion 144.

Figure 12:
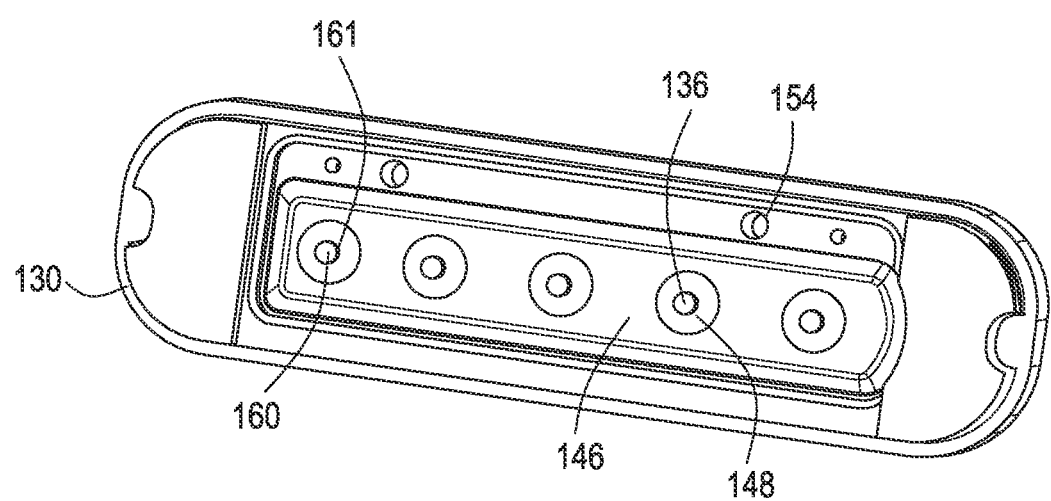
FIG. 12 shows a bottom view of the connector enclosure assembly with the support body removed to reveal the filter cap.

FIG. 12 shows the underside of the base plate 130 and the filter capacitor 146 with the support body 128 omitted for purposes of illustration. Here, the cavities 154 in the base plate 130 can be seen that receive the posts 164 of the support body 128. Another feature that can be seen in FIG. 12 is the asymmetrical shape of the filter capacitor 146 in this example, where one end is square and the opposite end is curved outwardly. The base plate 130 has a matching asymmetrical recess which prevents the filter capacitor 146 from being inserted in the wrong orientation. For embodiments where one of the apertures of the filter capacitor 146 is a ground aperture 161 where the ground plates 170 are present, this is significant because this prevents the ground aperture 161 from being aligned with a feedthrough pin 136 because the ground pin 160 should be present in the ground aperture 161 rather than a feedthrough pin 136.

Figure 13:
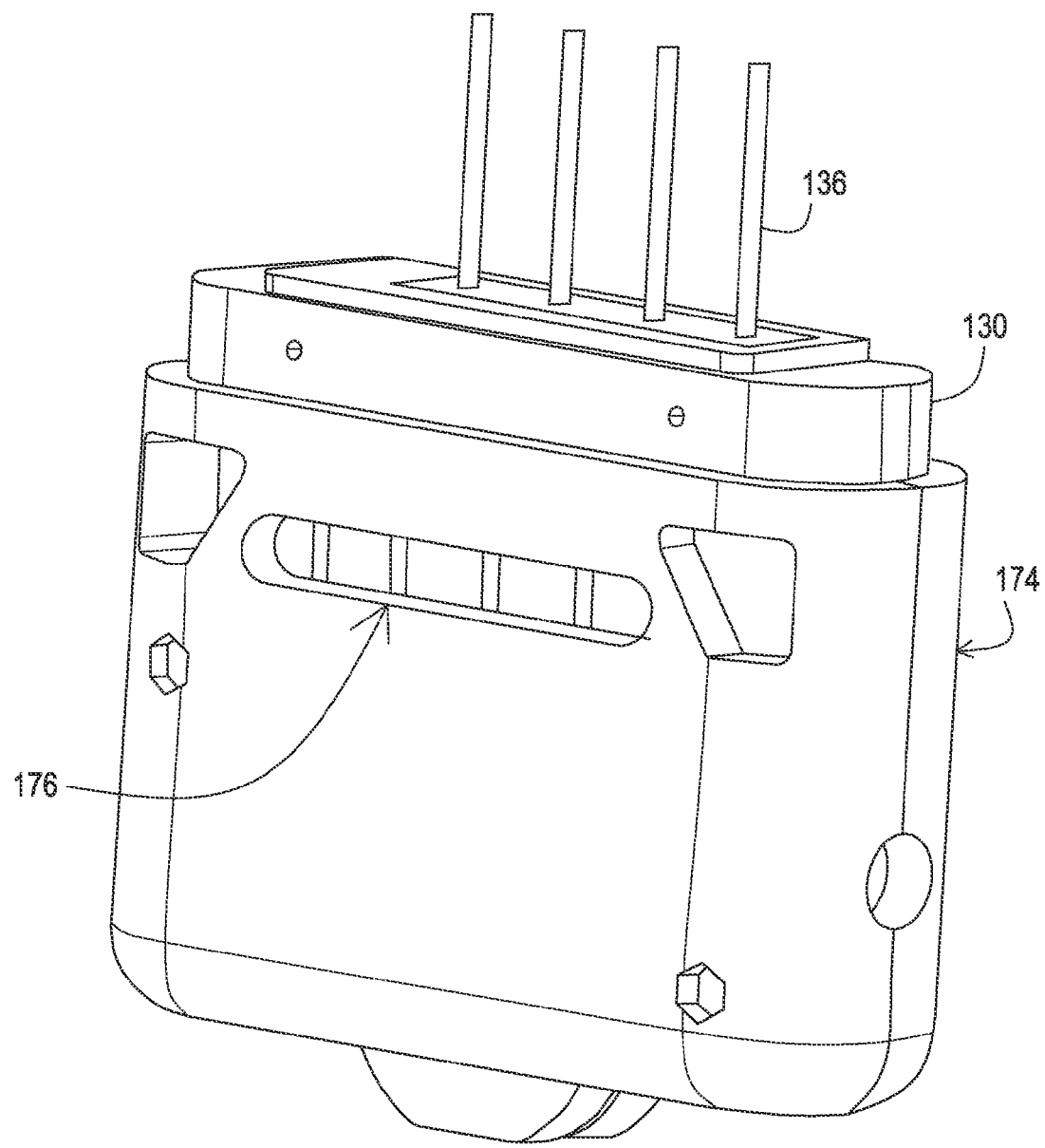
FIG. 13 shows a view of the base plate portion of the connector enclosure assembly with a protective body attached thereto.

FIG. 13 shows a protective body 174 that is attached to a partial connector enclosure assembly that includes the base plate 130 and the feedthrough pins 136, as well as the filter capacitor 146, support body 128, and conductors 126 within the protective body 174. The protective body 174 protects the underside of the base plate 130, particularly the exposed conductors 126 that are intended to extend into the can of the IMD 102, during the construction, testing, transporting, and storage of the connector enclosure assembly 106. The protective body 174 may be constructed of various rigid materials but where electrical testing is desired, the protective body 174 is constructed of an insulator such as liquid crystal polymer to avoid short circuiting across the conductors 126.

Figure 14:
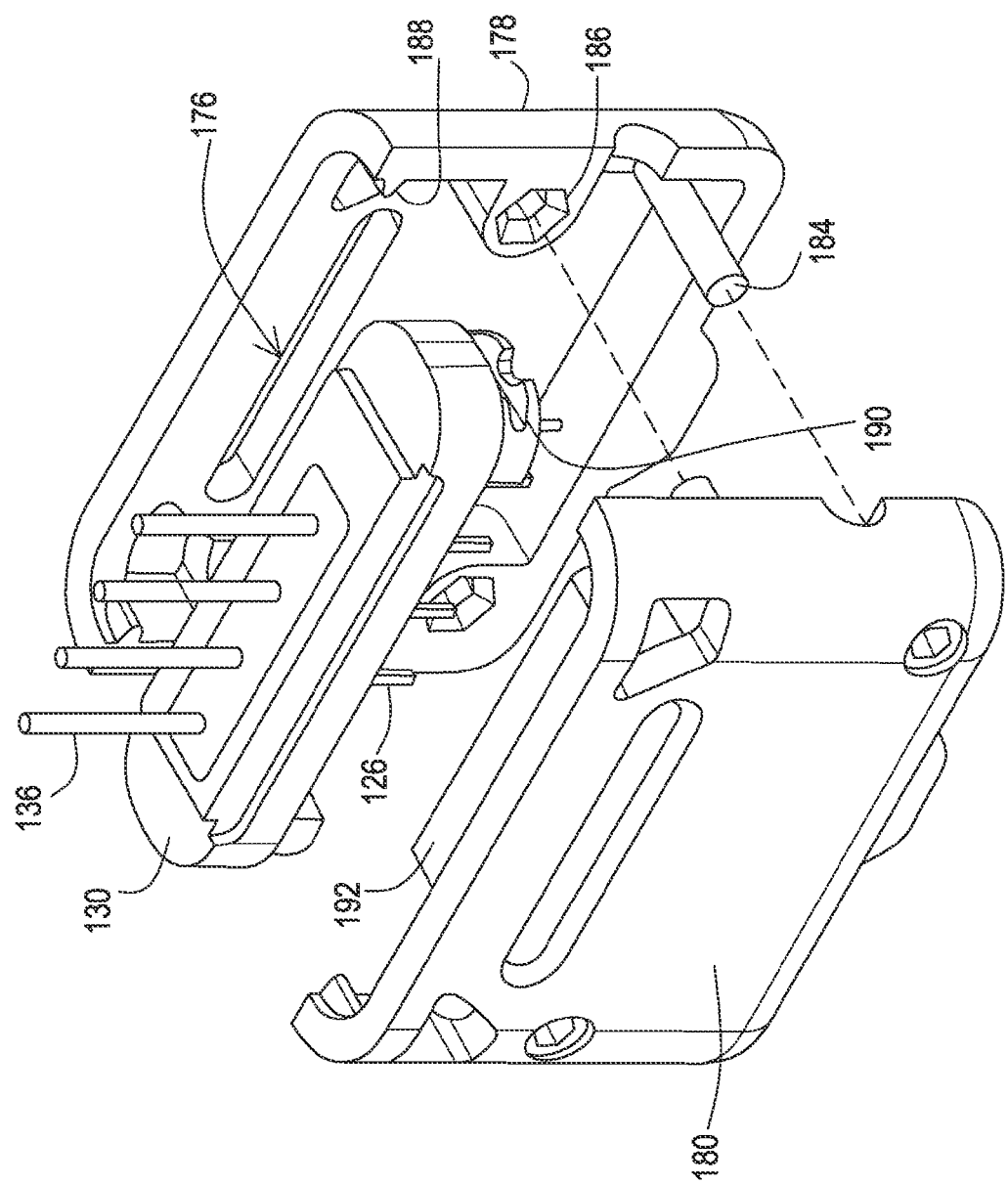
FIG. 14 shows an exploded view of the protective body.

The protective body 174 includes a window 176 that exposes the conductors 126 so that electrical connection may be made to test the electrical pathway between the conductors 126 and the individual electrical connectors 132 as shown in FIG. 3. As shown in FIG. 14, the protective body 174 may include two halves, a half 180 and another half 178. In this example, a window 176 exists within the half 174 for access to the conductors 126.

The protective body 174 may also includes features that allow the two halves 178, 180 to be joined together while engaging the base plate 130. For instance, posts 184 and receptacles 186 may be provided where the posts are press fit into the receptacles as a flange 188 of each half slides into place within a groove 190 on the base plate 130. This locks the two halves 178, 180 together while locking the body 174 to the base plate 130.

Figure 15:
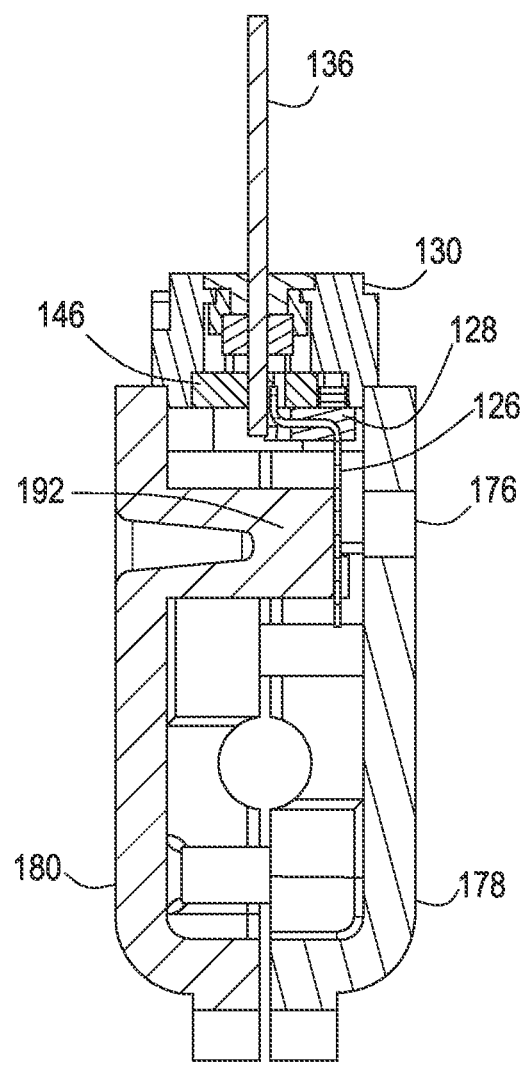
FIG. 15 shows a front-to-back cross-sectional view of the base plate and protection body.

FIG. 15 shows a cross-sectional view which shows the relationship of an extended support 192 to the conductor 126. The support 192 extends over to the conductor 126 so as to provide a stop against movement of the conductor 126. Thus, the conductor 126 is protected from excessive movement that could bend or break the conductor 126 such as during assembly, testing, transport, and/or storage.

Figure 16:
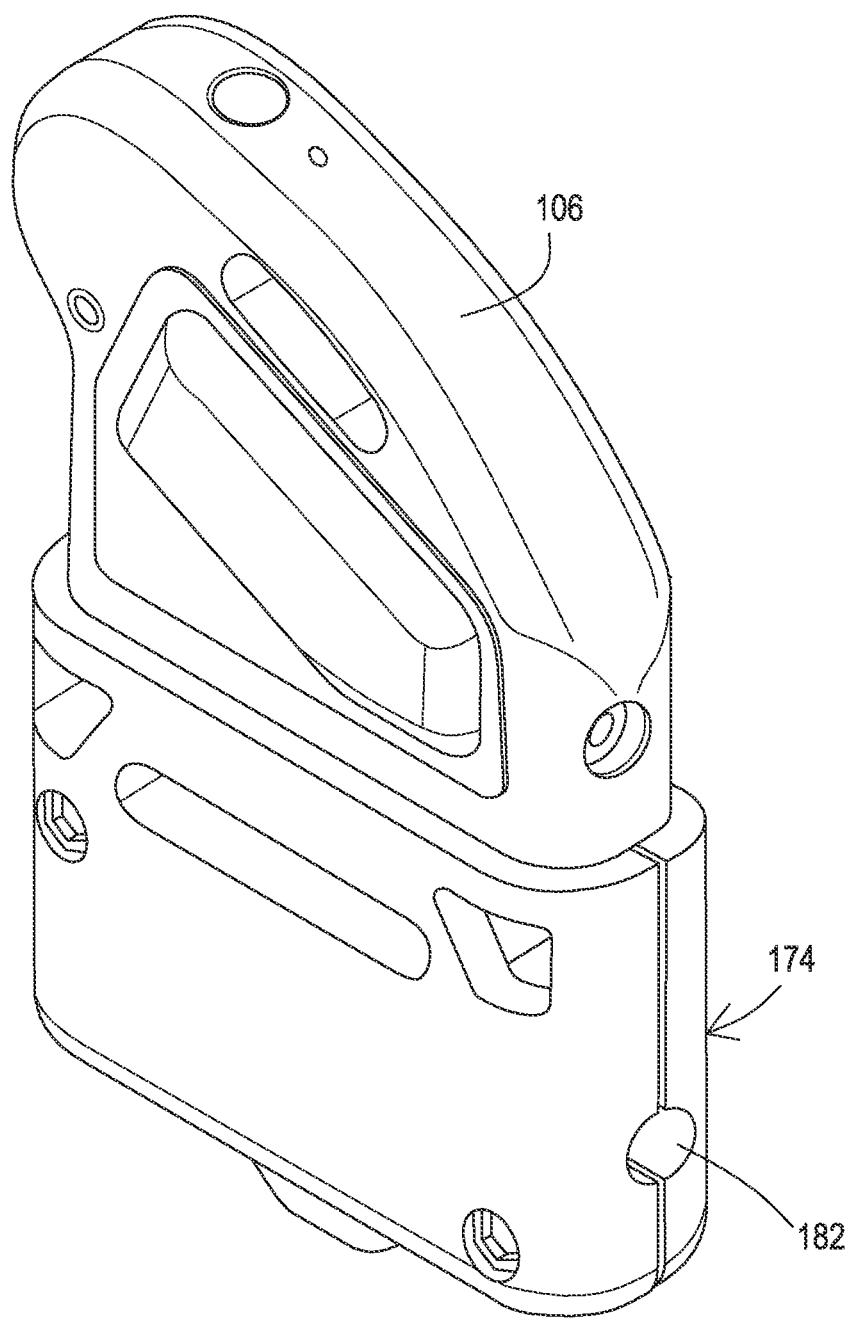
FIG. 16 shows a view of the connector enclosure assembly with the protective body attached thereto.

FIG. 16 shows the completed connector enclosure assembly 106 with the protective body 174 being attached to the base plate 130 of the connector enclosure assembly 106. At this point, the connector enclosure assembly 106 is ready for testing, transport, and storage while the can portion of the IMD 102 is being readied for attachment to the connector enclosure assembly 106. When the time arrives for attachment, the protective cover 174 is broken open using the holes 182 that are on both sides of the protector halves 178 & 180. The assembly process of the IMD 102 then proceeds.

One manner of assembling the IMD 102 that includes the features discussed above follows. It will be appreciated that this manner of assembly is for illustrative purposes and that other manners of assembling the IMD 102 are also possible. Initially in this example, the inner region where the feedthrough apertures 138 are located is welded in place to an outer structure of the baseplate to complete the baseplate assembly 130. The inner region contains the feedthrough pins 136 passing through the ferrules 140 filled with the nonconductive polymer 141 and with the insulator 158 being located underneath the ferrule 140.

The filter capacitor 146 is then inserted with each feedthrough pin 136 passing through an aperture 142. The support body 128 with the conductors 126 present therein is then positioned so that each conductor 126 enters the region 144 of the aperture 142. The support body 148 is then pressed into place such that the mounting posts 164 firmly lock into the cavities 154 of the baseplate 130.

At this point, the feedthrough pins 136, conductors 126, and filter capacitor 146 may be bonded by placing the solder split performs 149 in place as shown in FIG. 5A. The filter capacitor 146 may also be bonded to the baseplate 130 at this time by placing a solder wire along the edge of the filter capacitor 146 between the filter capacitor 146 and the base plate 130. The solder wire 150 and solder split performs 149 are then reflowed to complete the partial connector enclosure assembly.

The protective cover 174 is then installed as shown in FIG. 13. Thermal, shock, and electrical testing may then be performed. The partial connector enclosure assembly is then ready for further assembly and may be transported and/or stored prior to the time to complete the assembly.

At the next step, the nonconductive polymer 141 is added to the ferrules 140 and then the medical adhesive 155 is applied to the top of the baseplate 130. The feedthrough pins 136 are formed as necessary to be in position to contact the electrical connectors 132. The pre-assembled set of electrical connectors 136, such as a Bal Seal® stack is then placed against the feedthrough pins 136 where they are then mechanically and electrically interconnected.

A top portion of the connector enclosure 106 is then placed onto the baseplate 130 and set of connectors 132. The set screw 134 is inserted into position within the top portion of the connector enclosure 106. A cover plate of the connector enclosure 106 that covers an open side of the top portion of the connector enclosure 106 is put in position on the top portion and against the baseplate 130. The top portion, cover plate, and the baseplate 130 are then seam welded, and the cavity within the connector enclosure 106 is filled with a non-conductive polymer by injection molding. At this point, the connector enclosure 106 is ready for final assembly of the IMD 102.

During final assembly, the isolation cup 118 is placed into the bottom half of the can 108 as shown in FIG. 2. The electrical circuitry 122 is then placed within the isolation cup 118, and the battery 120 is also positioned within the isolation cup 118.

The protective cover 174 is broken open to allow the connector enclosure assembly 106 to be removed from the protective cover 174. The connector enclosure assembly 106 is then placed over the bottom half of the can 108 and the conductors 126 are mechanically and electrically connected to the electrical pads 124.

The bottom cap 116 is then added to the bottom half of the can 108. The top half of the can 108 is then placed into position relative to the bottom half. The interfaces of the two halves of the can 108, the bottom cap 116, and the baseplate 130 of the connector assembly 106 are seam welded to complete the assembly of the IMD 102.

Figure 17:
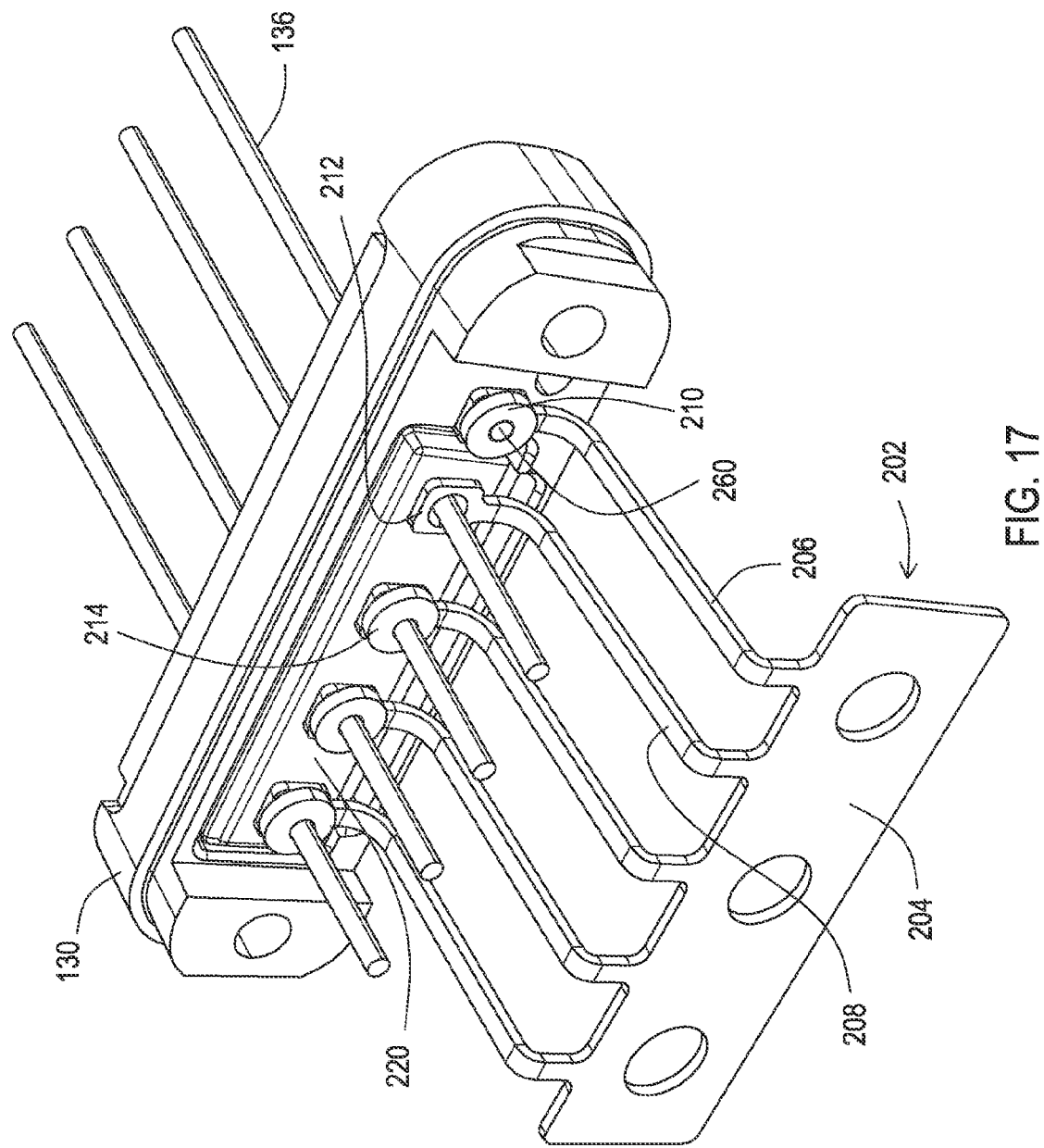
FIG. 17. shows a view of an embodiment where conductors are joined at a common tab and positioned for mounting to the feedthrough pins.

FIG. 17 shows another embodiment of an interconnection of a filtered feedthrough. Here the feedthrough pins 136 pass through apertures in the baseplate 130 and through a filter capacitor 220 as discussed for the prior embodiments. However, in this embodiment, the interconnection of the feedthrough pins 136 to the pads on the hybrid of the circuitry within the can is ultimately provided by conductors 206, 208. In this particular embodiment, these conductors 206, 208 are held in a fixed position with respect to one another prior to being installed by being formed together as an integral conductor unit 202 where each conductor 206, 208 extends from a common tab 204. The integral conductor unit 202 may be constructed of materials such as titanium, nickel, niobium, tantalum, platinum, MP35N® alloy, or other alloys thereof. Furthermore, the integral conductor unit 202 may include an outer layer that is plated or sputtered with material such as noble metals like gold or platinum to allow solder wetting to the conductor 206, 208 to occur during the soldering process.

The common tab 204 allows the integral conductor unit 202 to be easily grasped and positioned during assembly of the structure shown in FIG. 17 while the conductors 206, 208 maintain their relative spacing and orientation. Each conductor 206, 208 extends from the common tab 204 at the proper spacing relative to the feedthrough pins 136 such that the conductors 206, 208 are more easily aligned and mated to the corresponding feedthrough pins 136.

In this particular embodiment, the ends of the conductors 206, 208 opposite the common tab 204 include annular rings such as the annular ring 212 revealed for the conductor 208. The feedthrough pins 136 pass through the openings of the annular rings 212. The annular rings are then secured to the feedthrough pins 136. In the case of the ground conductor 206, the annular ring is secured to a ground pin 260 of the baseplate 130. Thereafter, the common tab 204 is removed from the conductors 206, 208 such as by cutting or breaking the conductors 206, 208 in vicinity of the common tab 204. For instance, the conductors 206, 208 may be formed with a thinner section near the common tab 204 which provides a weak area that facilitates the cut or break.

There may be several ways to secure the conductors 206, 208 to the ground pin 260 or feedthrough pins 136. For instance, in some embodiments, the conductors 206, 208 may be soldered to the respective pin. As shown in FIG. 17, a pre-formed solder washer 210, 214 may be positioned about the pin and onto the annular ring and then reflowed to create a bond that forms the physical and electrical coupling of the conductors 206, 208 to the pins. The solder washer for the annular ring 212 has been omitted from FIG. 17 for purposes of illustrating the annular ring but would be included to provide the bond.

Figure 18:
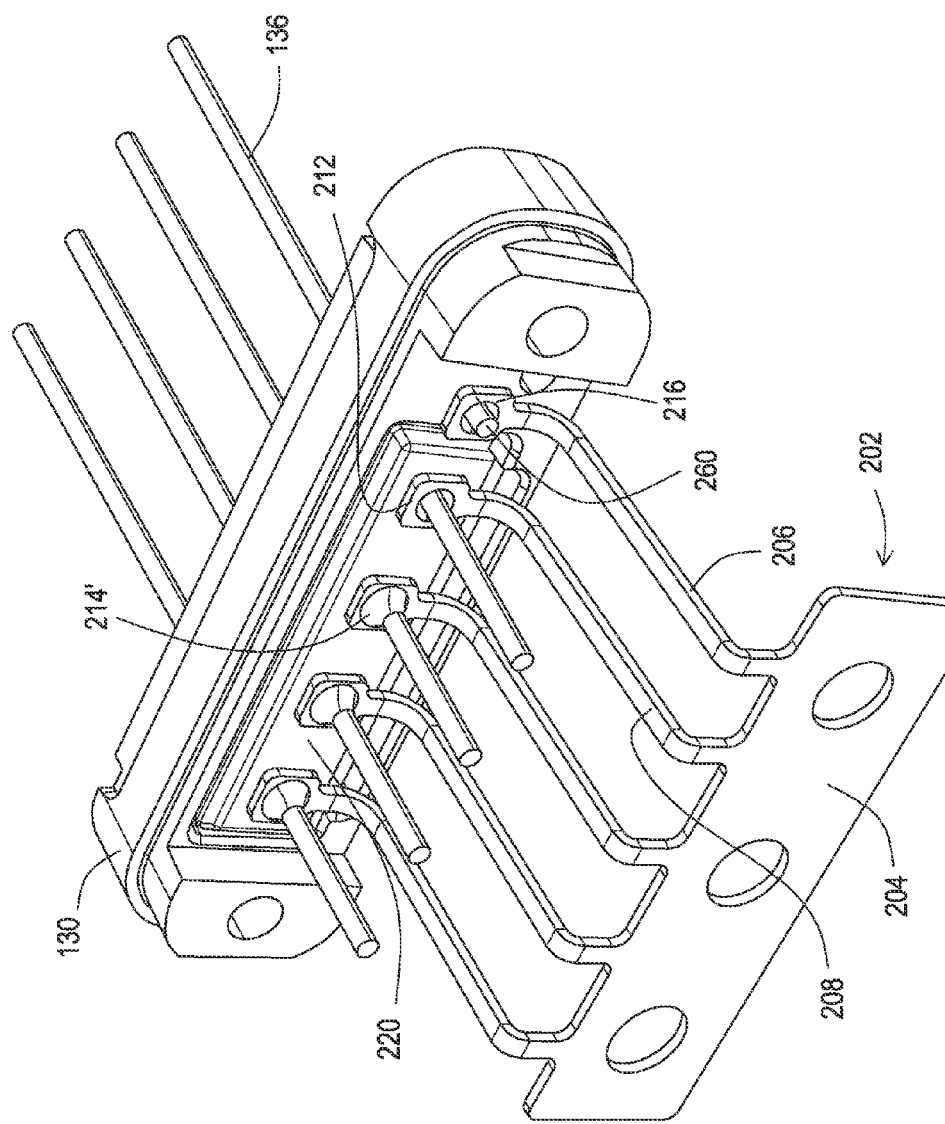
FIG. 18 shows a view of the embodiment where the conductors that are joined at the common tab being soldered.

FIG. 18 shows the interconnection of some of the conductors to some of the feedthrough pins 136 once the solder has been reflowed to create the bond 214'. FIG. 18 also omits the washer 210 for the ground pin 260 to more clearly illustrate the ground pin 260 in relation to the annular ring 216 of the ground conductor 206. The reflowed solder 214' of FIG. 18 also flows into the opening of the filter capacitor 220 to create an electrical coupling of the feedthrough pin 136 to a capacitor plate within the filter capacitor 220. While FIG. 18 shows the feedthrough pins 136 as extending well beyond the annular rings 212, it will be appreciated that the feedthrough pins 136 may be trimmed to the appropriate length before or after the soldering has occurred in order to achieve the final version shown in FIG. 21 which is discussed below.

Some embodiments of the annular rings 212 may include extensions and the filter capacitor 220 may include keyhole shaped openings like that of FIGS. 5B and 11 such that the extensions of the annular rings 212 enter the keyhole area and are further soldered to the pin and capacitor plate. Likewise, for the embodiments discussed above with respect to FIGS. 5B and 10, those conductors 126, 162 may include annular rings that are positioned about the feedthrough pins as shown in FIGS. 17 and 18.

Figure 19:
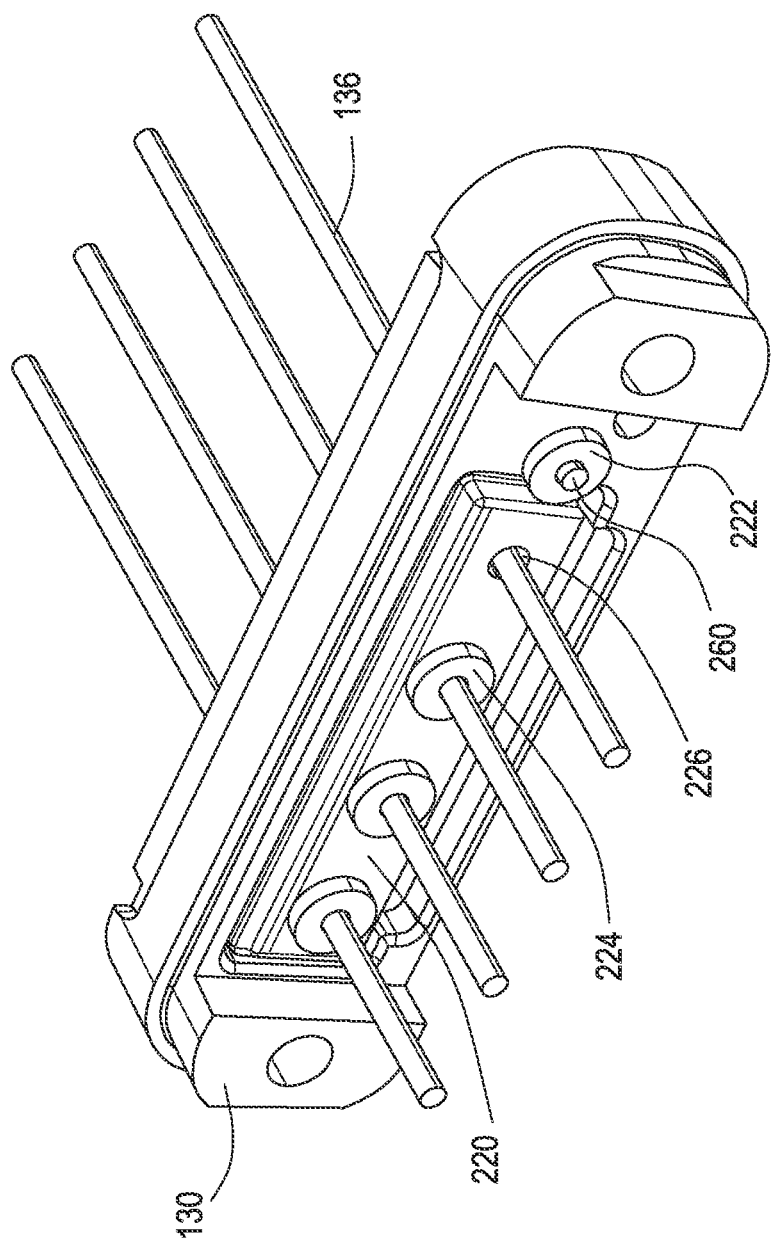
FIG. 19 shows an embodiment where washers are positioned about the feedthrough pins.
Figure 20:
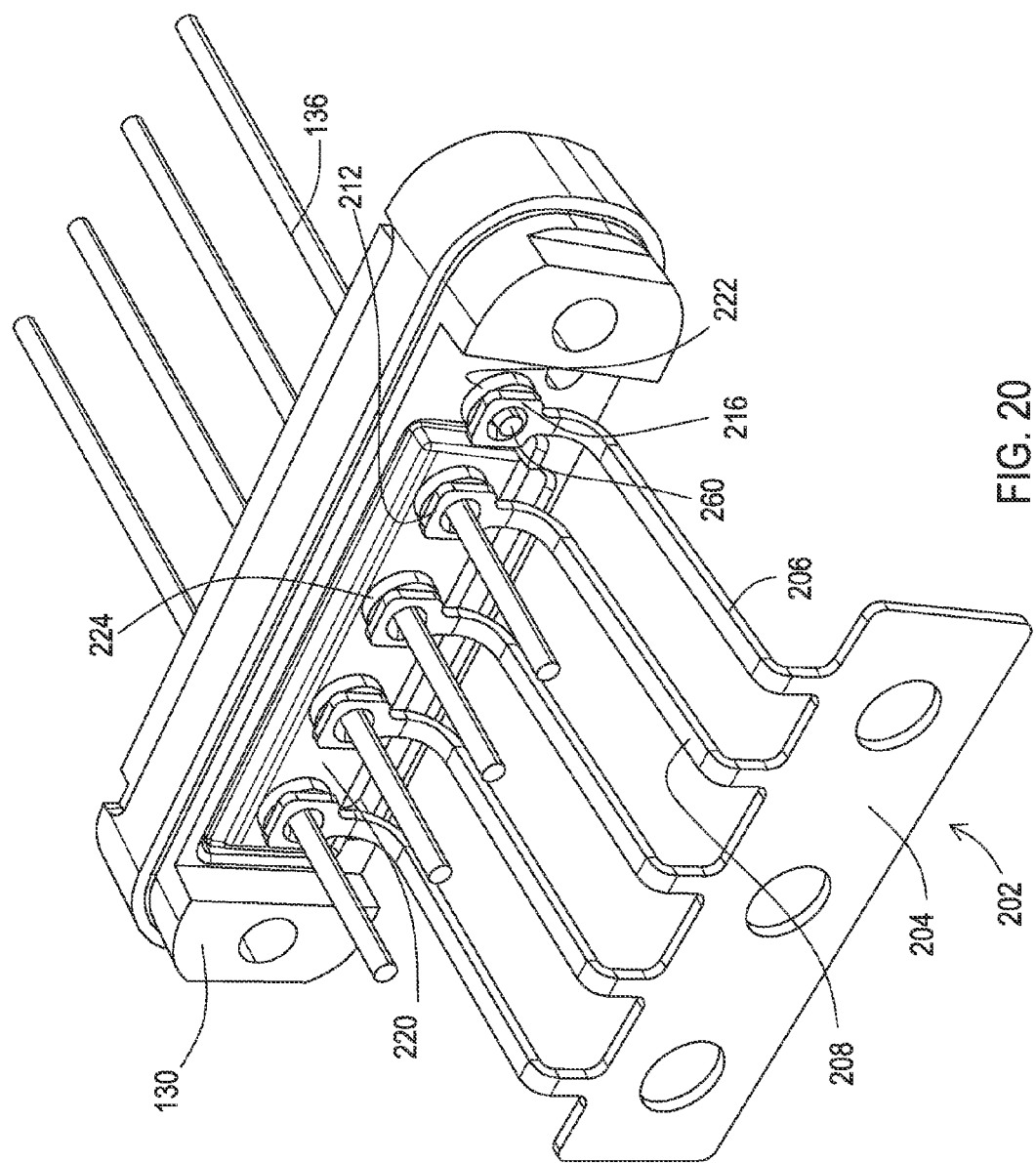
FIG. 20 shows the embodiment where the conductors that are joined at the common tab are positioned at the washers for mounting to the feedthrough pins.

An alternative manner of securing the conductors 206, 208 to the pins is shown in FIG. 19. Here, the bond of the conductors 206, 208 to the pins 260, 136 is created by welding. In order to protect the filter capacitor 220, protective washers 222, 224 are placed about the ground pin 260 and feedthrough pins 136, respectively. These protective washers may be constructed of a material such as alumina or glass to create an effective barrier. However, prior to installation of the washers, the feedthrough pins 136 are soldered to the capacitive plates of the filter capacitor 220 by flowing solder into the openings 226 of the filter capacitor 220. Then, the protective washers 222, 224 are put in place, followed by placement of the annular rings of the conductors 206, 208 about the pins 260, 136. The annular rings are then welded to the pins 260, 136. This configuration is illustrated in FIG. 20. While FIG. 20 shows the feedthrough pins 136 as extending well beyond the annular rings 212, it will be appreciated that the feedthrough pins 136 may be trimmed to the appropriate length before welding has occurred in order to achieve the final version like that shown in FIG. 23 which is discussed below.

Figure 21:
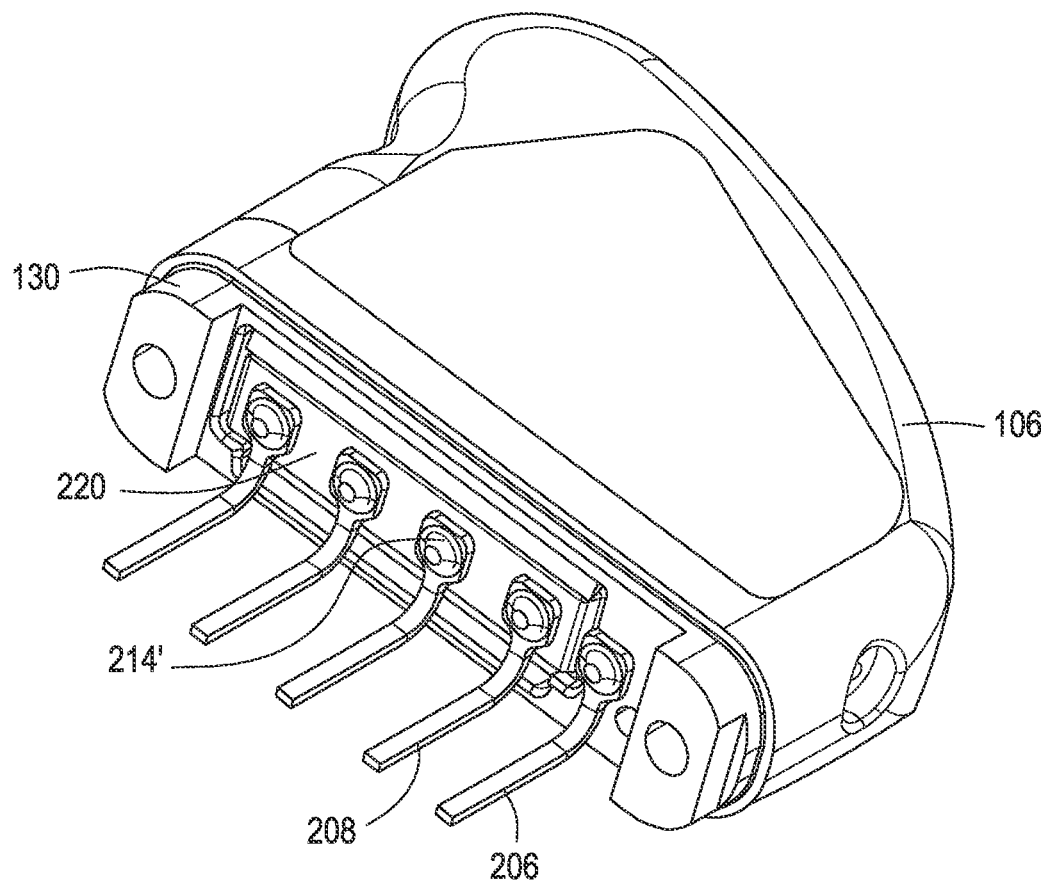
FIG. 21 shows a connector enclosure assembly with the conductors soldered in place and the common tab removed.

A completed connector enclosure assembly 106 is shown in FIG. 21. Here, the annular rings of the conductors 206, 208 have been bonded to the ground pin 260 and feedthrough pins 136, such as by reflowing solder 214' as shown, and the common tab 204 has been broken free and discarded. At this point, the conductors 206, 208 are ready to be bonded to pads of the hybrid.

Figure 22:
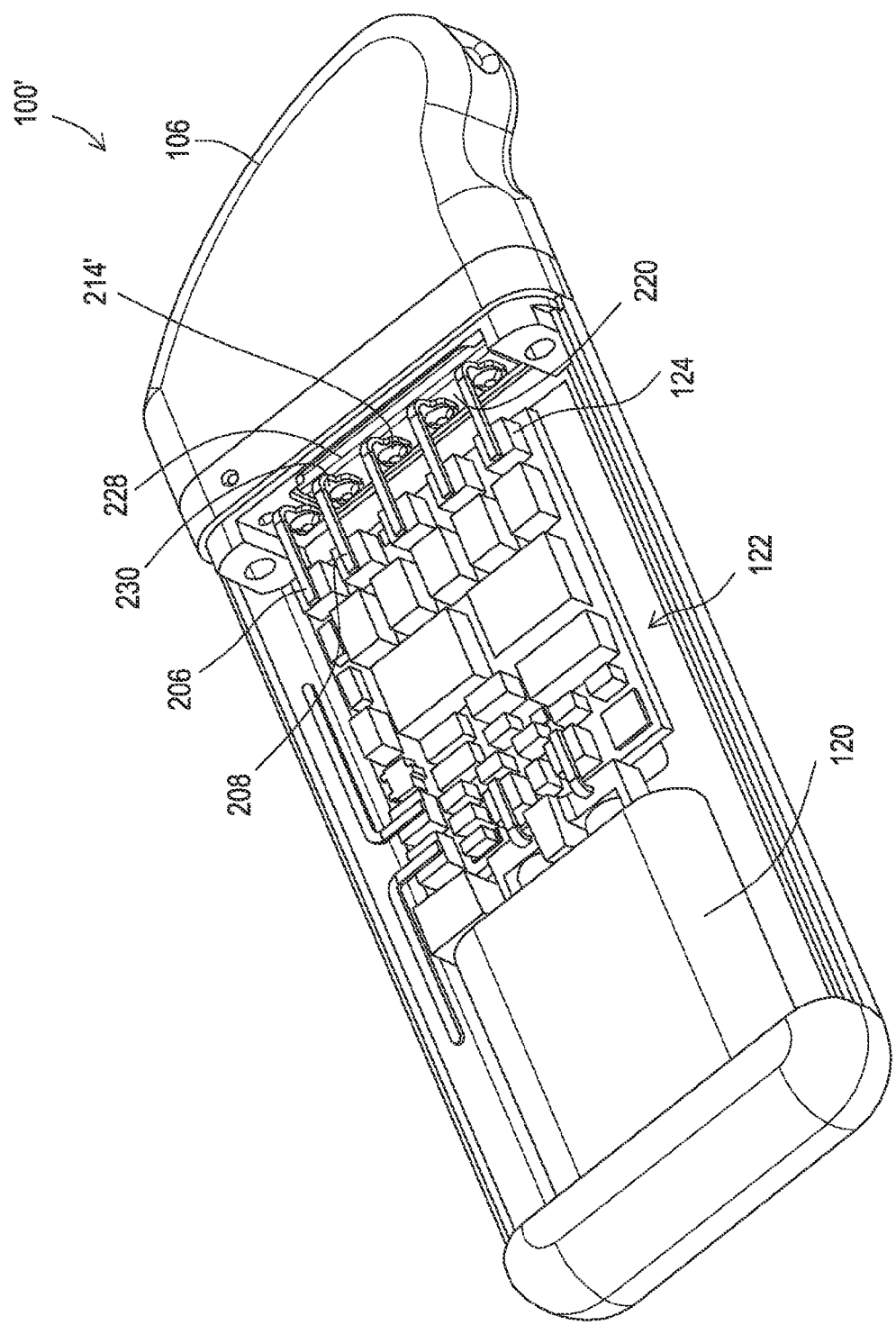
FIG. 22 shows the connector assembly being attached to a remainder of a medical device after the common tab has been removed from the conductors.

FIG. 22 shows the connector enclosure assembly 106 upon being joined to the hybrid circuitry 122 during assembly of the medical device 100'. In this particular example, the baseplate 130 has been bonded to one half of the can while the conductors 206, 208 have been soldered to pads 124 of the hybrid to complete the physical and electrical coupling of the conductors 206, 208 to the hybrid. As discussed above for other embodiments, other manners of constructing the device 100' are also possible, such as constructing the whole can separately, bonding the conductors 206, 208 to the pads 124, and then inserting the hybrid circuitry 122 into the assembled can while bonding the baseplate 130 to the assembled can.

Figure 23:
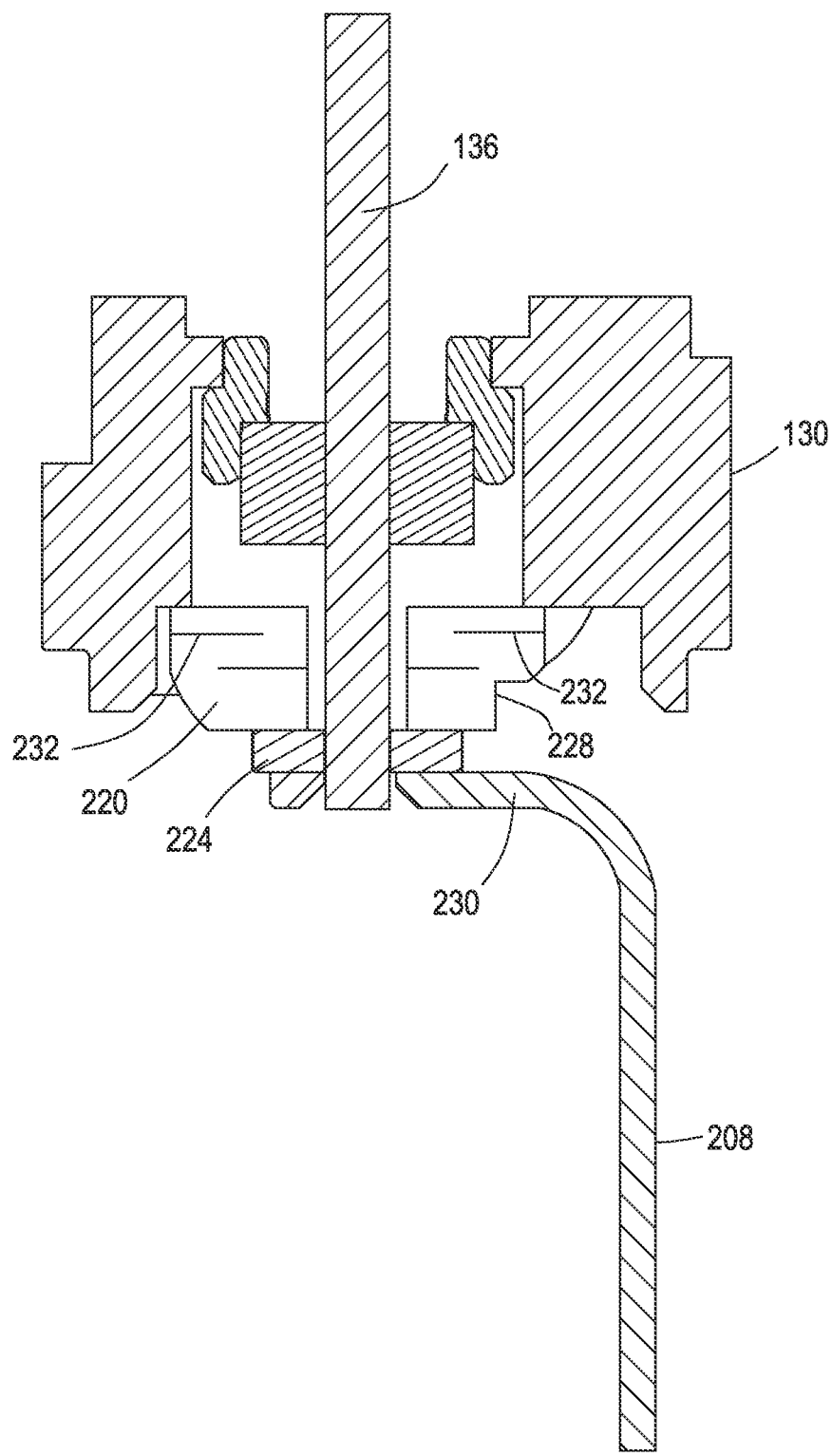
FIG. 23 shows a cross-sectional view of an embodiment where conductors are joined to feedthrough pins at a filter capacitor and the filter capacitor includes a notch.

Another aspect that is present in the embodiment shown in FIG. 22 as a recess 228 within the filter capacitor 220 in proximity to a transitional section 230 of each conductor 208, where the transactional section extends from the annular ring to where the conductor 208 becomes approximately perpendicular to the plane of the filter capacitor 220. As shown in FIG. 23, the ground plate 232 of the filter capacitor 220 is exposed at the outer edges so that soldering electrically couples the ground plate 232 to the baseplate 130. Furthermore, the ground plate 232 may terminate to a metallic layer such as silver-palladium on the exterior side of the filter capacitor 220 that further allows the filter capacitor 220 to be soldered to the baseplate 130.

To ensure that the transitional area 230 of each conductor 208 does not electrically short circuit to ground, the notch 228 is present in the filter capacitor 220 to create additional airspace between the exposed area of ground plate 232 where the ground plate 232 and any metallic layer on the outer surface is soldered and the transitional area 230. While FIG. 23 shows an example where the annular ring has been welded to the pin 136 with the protective washer 224 in place, it will be appreciated that his configuration of the filter capacitor 220 with the notch 228 is also applicable to examples where the annular ring is soldered to the feedthrough pin 136.

While embodiments have been particularly shown and described, it will be understood by those skilled in the art that various other changes in the form and details may be made therein without departing from the spirit and scope of the invention.

What is claimed is:

1. An implantable medical device, comprising:
a connector enclosure including a base plate having an aperture, the connector enclosure housing at least one electrical connector;
a can coupled to the base plate, the can housing electrical circuitry;
a filter capacitor coupled to the base plate, the filter capacitor having an aperture and having capacitor forming plates including a ground plate, the ground plate being electrically coupled to the can;
a feedthrough pin electrically coupled to the electrical connector within the connector enclosure, the feedthrough pin extending through the aperture in the base plate and being electrically coupled to at least one filter capacitor;
a support body having a coupling to the base plate, the support body having a conductor passing through, the conductor having a first end extending from the support body on one side and a second end extending from the support body on another side, the first end being electrically coupled to the filter capacitor and the feedthrough pin and the second end extending into the can and being electrically coupled to the electrical circuitry.

2. The implantable medical device of claim 1, further comprising an electrically conductive bonding material being present within the aperture of the filter capacitor and creating an electrically conductive bond among the conductor, the feedthrough pin, and at least one of the capacitor forming plates other than the ground plate.

3. The implantable medical device of claim 2, wherein the bonding material is solder.

4. The implantable medical device of claim 2, wherein the second end of the conductor is directly bonded to a circuit board within the can that contains the electrically circuitry.

5. The implantable medical device of claim 2, wherein the filter capacitor has an asymmetric shape and wherein the base plate includes a recess that defines an asymmetric shape that matches the asymmetric shape of the filter capacitor.

6. The implantable medical device of claim 2, wherein the aperture within the filter capacitor has a keyhole shape and wherein the feedthrough pin and the conductor pass into the aperture within the filter capacitor.

7. The implantable medical device of claim 1, wherein the support body includes posts and the base plate includes cavities and wherein the posts are contained within the cavities.

8. A connector enclosure assembly for an implantable medical device, comprising:
a connector enclosure including a base plate having an aperture, the connector enclosure housing at least one electrical connector;
a filter capacitor coupled to the base plate, the filter capacitor having an aperture and having capacitor forming plates;
a feedthrough pin electrically coupled to the electrical connector within the connector enclosure, the feedthrough pin extending through the aperture in the base plate and being present in the vicinity of the aperture in the filter capacitor;
a conductor with a first end being present in the vicinity of the aperture within the filter capacitor and with a second end extending away from the filter capacitor, the first end being electrically coupled to the filter capacitor and the feedthrough pin; and
a protector body affixed to the base plate, the protector body enclosing the conductor while having an aperture providing access to the conductor.

9. The connector enclosure assembly of claim 8, wherein the protector body includes a first portion and a second portion, the first portion having features that mate to features of the second portion such that the protector body is attached by the first portion and second portion being individually engaged to the base plate and the features of the first portion being mated to the features of the second portion.

10. The connector enclosure assembly of claim 9, wherein the aperture is defined by an aperture in the first portion and an aperture in the second portion that is aligned with the aperture in the first portion upon mating the features of the first portion to the features of the second portion.

11. The connector enclosure assembly of claim 10, wherein the support body includes posts and the base plate includes cavities and wherein the posts are contained within the cavities.

12. The connector enclosure assembly of claim 8, further comprising providing a support body that is coupled to the base plate, wherein the conductor passes through the support body.

13. The connector enclosure assembly of claim 8, further comprising an electrically conductive bonding material being present within the aperture of the filter capacitor and creating an electrically conductive bond among the conductor, the feedthrough pin, and at least one of the capacitor forming plates.

14. The connector enclosure assembly of claim 13, wherein the electrically conductive material is solder.

15. The connector enclosure assembly of claim 8, wherein the filter capacitor has an asymmetric shape and wherein the base plate includes a recess that defines an asymmetric shape that matches the asymmetric shape of the filter capacitor.

16. A connector enclosure assembly for an implantable medical device, comprising:
a connector enclosure including a base plate having a plurality of apertures;
a filter capacitor coupled to the base plate, the filter capacitor having a plurality of apertures and having capacitor forming plates;
a plurality of feedthrough pins extending through the apertures in the base plate and in the filter capacitor; and
a plurality of conductors with a first end of each conductor having an annular ring that surrounds a corresponding feedthrough pin in proximity to the filter capacitor with a second end of the plurality of conductors extending away from the filter capacitor and being joined to a common tab that is separated from the filter capacitor.

17. The connector enclosure assembly of claim 16, wherein the annular ring of each of the conductors is soldered to the corresponding feedthrough pin.

18. The connector assembly of claim 16, wherein the annular ring of each of the conductors is welded to the corresponding feedthrough pin.

19. The connector assembly of claim 18, further comprising a plurality washers with a washer of the plurality being positioned about a corresponding feedthrough pin between the filter capacitor and the annular ring of the conductor.

20. The connector assembly of claim 16, wherein each of the conductors has a transitional area and where the filter capacitor has a notch in proximity of the transitional area.

21. A method of manufacturing a connector enclosure assembly of an implantable medical device, comprising:
providing a connector enclosure including a base plate having a plurality of apertures;
providing a filter capacitor coupled to the base plate, the filter capacitor having a plurality of apertures and having capacitor forming plates;
providing a plurality of feedthrough pins extending through corresponding apertures in the base plate and in the filter capacitor; and
positioning a plurality of conductors with a first end of each conductor having an annular ring that surrounds a corresponding feedthrough pin in proximity to the filter capacitor with a second end of the plurality of conductors extending away from the filter capacitor and wherein the plurality of conductors are positioned by the second ends having a connection to a common tab that is separated from the filter capacitor.

22. The method of claim 21, further comprising soldering the annular rings to the corresponding feedthrough pins.

23. The method of claim 21, further comprising welding the annular rings to the corresponding feedthrough pins.

24. The method of claim 23, further comprising positioning a plurality of washers about corresponding feedthrough pins between the filter capacitor and the annular rings of the conductors.

25. The method of claim 21, further comprising breaking the common tab free from the second ends of the conductors.

26. A connector enclosure assembly for an implantable medical device, comprising:
a connector enclosure including a base plate having a plurality of apertures;
a filter capacitor coupled to the base plate, the filter capacitor having a plurality of apertures and having capacitor forming plates;
a plurality of feedthrough pins extending through the apertures in the base plate and in the filter capacitor;
a plurality of conductors with a first end of each conductor having an annular ring that surrounds a corresponding feedthrough pin in proximity to the filter capacitor with a second end of the plurality of conductors extending away from the filter capacitor and being joined to a common tab; and
a plurality of washers with a washer of the plurality being positioned about a corresponding feedthrough pin between the filter capacitor and the annular ring of the conductor.

27. A method of manufacturing a connector enclosure assembly of an implantable medical device, comprising:
providing a connector enclosure including a base plate having a plurality of apertures;
providing a filter capacitor coupled to the base plate, the filter capacitor having a plurality of apertures and having capacitor forming plates;
providing a plurality of feedthrough pins extending through corresponding apertures in the base plate and in the filter capacitor;
positioning a plurality of conductors with a first end of each conductor having an annular ring that surrounds a corresponding feedthrough pin in proximity to the filter capacitor with a second end of the plurality of conductors extending away from the filter capacitor and wherein the plurality of conductors are positioned by the second ends having a connection to a common tab; and
breaking the common tab free from the second ends of the conductors.

* * * * *

UNITED STATES PATENT AND TRADEMARK OFFICE
CERTIFICATE OF CORRECTION

PATENT NO. : 9,597,518 B2  
APPLICATION NO. : 13/981274  
DATED : March 21, 2017  
INVENTOR(S) : Deininger et al.

Page 1 of 1

It is certified that error appears in the above-identified patent and that said Letters Patent is hereby corrected as shown below:

Column 15, Line 49 in Claim 19: "comprising a plurality washers" should read --comprising a plurality of washers--

Signed and Sealed this  
Tenth Day of April, 2018

Andrei Iancu  
*Director of the United States Patent and Trademark Office*